(12) United States Patent
Komplin et al.

(10) Patent No.: US 7,335,800 B2
(45) Date of Patent: Feb. 26, 2008

(54) HYDROGENATION CATALYST AND HYDROGENATION METHOD

(75) Inventors: Glenn Charles Komplin, Katy, TX (US); John Anthony Smegal, Houston, TX (US)

(73) Assignee: Shell Oil Company, Houston, TX (US)

( * ) Notice: Subject to any disclaimer, the term of this patent is extended or adjusted under 35 U.S.C. 154(b) by 168 days.

(21) Appl. No.: 11/409,433

(22) Filed: Apr. 21, 2006

(65) Prior Publication Data

US 2006/0241325 A1 Oct. 26, 2006

Related U.S. Application Data

(60) Provisional application No. 60/673,530, filed on Apr. 21, 2005.

(51) Int. Cl.
  C07C 29/14 (2006.01)
  B01J 21/08 (2006.01)
  B01J 23/28 (2006.01)

(52) U.S. Cl. ............... 568/862; 568/880; 568/881; 568/882; 568/883; 568/914; 502/257; 502/240; 502/254; 502/255

(58) Field of Classification Search ............... 568/862, 568/880, 881, 882, 883, 914; 502/257, 240, 502/254, 255
See application file for complete search history.

(56) References Cited

U.S. PATENT DOCUMENTS

| | | | |
|---|---|---|---|
| 2,434,110 A | 1/1948 | Hatch et al. ............... 260/602 |
| 3,068,303 A | 12/1962 | Pattison ..................... 260/677 |
| 3,098,882 A | 7/1963 | Arnold ....................... 260/677 |
| 3,109,804 A | 11/1963 | Martin ........................ 208/89 |
| 3,205,281 A | 9/1965 | Fleming et al. ............. 260/683 |
| 3,260,759 A | 7/1966 | Skinner ..................... 260/677 |
| 3,296,325 A | 1/1967 | Gross ........................ 260/677 |
| 4,912,260 A | 3/1990 | Dobson et al. ............. 564/480 |
| 5,015,789 A | 5/1991 | Arntz et al. ................ 568/862 |
| 5,093,537 A | 3/1992 | Unruh et al. ............... 568/862 |
| 5,210,318 A | 5/1993 | Briggs et al. ............... 568/496 |
| RE34,349 E | 8/1993 | Unruh et al. ............... 568/862 |
| 5,256,827 A | 10/1993 | Slaugh et al. .............. 568/454 |
| 5,334,778 A | 8/1994 | Haas et al. ................. 568/862 |
| 5,358,633 A | 10/1994 | Dai et al. ............... 208/216 R |
| 5,364,984 A | 11/1994 | Arntz et al. ................ 568/862 |
| 5,389,595 A | 2/1995 | Simpson et al. ............ 502/315 |
| 5,449,653 A | 9/1995 | Briggs et al. ............... 502/166 |
| 5,773,657 A | 6/1998 | Rutter et al. ............... 564/450 |
| 5,786,524 A | 7/1998 | Powell et al. .............. 568/862 |
| 5,814,112 A | 9/1998 | Elliott et al. ............. 48/197 R |
| 5,817,594 A | 10/1998 | McNamara et al. ........ 502/313 |
| 5,888,380 A | 3/1999 | Fujita et al. ............. 208/251 H |
| 5,910,241 A | 6/1999 | McNamara et al. ..... 208/251 H |
| 5,916,838 A | 6/1999 | Wulff-Doring et al. ..... 502/326 |
| 5,936,126 A | 8/1999 | Ruhl et al. ................. 564/451 |
| 5,945,570 A | 8/1999 | Arhancet et al. ........... 568/862 |
| 5,958,825 A | 9/1999 | Wulff-Doring et al. ..... 502/300 |
| 5,977,013 A | 11/1999 | Elliott et al. ............... 502/337 |
| 6,152,975 A | 11/2000 | Elliott et al. .............. 48/197 R |
| 6,232,511 B1 | 5/2001 | Haas et al. ................. 568/862 |
| 6,342,464 B1 | 1/2002 | Arhancet et al. ........... 502/257 |
| 6,376,720 B1 | 4/2002 | Han ........................... 568/483 |
| 6,399,538 B1 | 6/2002 | Hucul ........................ 502/325 |
| 6,429,167 B1 | 8/2002 | Maeno et al. .............. 502/325 |
| 6,670,300 B2 | 12/2003 | Werpy et al. ............... 502/182 |
| 6,911,566 B2 | 6/2005 | Tsunoda et al. ............ 568/862 |
| 2002/0087036 A1 | 7/2002 | Haas et al. ................. 568/885 |
| 2004/0097764 A1 | 5/2004 | Tsunoda et al. ............ 568/860 |
| 2004/0225161 A1 | 11/2004 | Sunkara et al. ............ 568/852 |
| 2004/0260125 A1 | 12/2004 | Seapan et al. ............. 568/868 |
| 2005/0033099 A1 | 2/2005 | Ryu et al. ................... 585/259 |
| 2005/0080300 A1 | 4/2005 | Komplin et al. ............ 568/862 |

FOREIGN PATENT DOCUMENTS

| | | |
|---|---|---|
| CN | 1122568 C | 5/1996 |
| CN | 1342521 | 4/2002 |
| CN | 1342633 | 4/2002 |
| CN | 1428190 | 7/2003 |
| CN | 1428322 | 7/2003 |

(Continued)

OTHER PUBLICATIONS

The Heterogeneous Oxidation of Hydrogen Sulfide at Concentrations Below 1000 ppm in Nitrogen/Air Mixtures Over Supported Metal Oxide Catalysts; W.G. Cook & R.A. Ross, *Atmospheric Environonment*, (1967-1989) 7(2), 145-151 (1973) Pergamon Press (1973).

Effects of Small MoO3 Additions on the Properties of Nickel Catalysts for the Steam Reforming of Hydrocarbons II. Ni-Mo/Al2O3 Catalysts in Reforming, Hydrogenolysis and Cracking of n-butane, *Applied Catalysis A*, General 230 (2002) 85-97.

(Continued)

*Primary Examiner*—Elvis O. Price
(74) *Attorney, Agent, or Firm*—Richard B. Taylor

(57) ABSTRACT

The present invention provides a hydrogenation catalyst effective for hydrogenating 3-hydroxypropionaldehyde to 1,3-propanediol. The hydrogenation catalyst comprises an α-alumina support, nickel, ruthenium, and a promoter. The nickel is deposited on the α-alumina support, and the ruthenium and the promoter are deposited on the nickel and the α-alumina support. The α-alumina support comprises at least 92 wt. % of the catalyst, and the nickel comprises from 1 wt. % to 6 wt. % of the catalyst. The present invention also provides a process of hydrogenating 3-hydroxypropionaldehyde to 1,3-propanediol with the catalyst.

32 Claims, 8 Drawing Sheets

FOREIGN PATENT DOCUMENTS

| | | |
|---|---|---|
| EP | 0906258 | 4/1999 |
| FR | 2191939 | 2/1974 |
| GB | 829475 | 3/1960 |
| GB | 966270 | 8/1964 |
| GB | 1011270 | 11/1965 |
| GB | 1436458 | 5/1976 |
| GB | 1581379 | 12/1980 |
| JP | 83049532 | 7/1979 |
| JP | 2004-182622 | 7/2004 |
| WO | 00/00456 | 1/2000 |

OTHER PUBLICATIONS

Oxidacion Deshidrogenate De Etilbenceno A Estrieno Sobre Oxidos De Molibdeno Y Niquel, H. Kum & J.L. Seane, *Anales De Quimica*, (1968-1979) 72(7-8), 703-708 (1976) (abstract).

Modification of 3-Hydroxypropanal Hydrogenation Catalyst, Z. Xu, S. Guo, J. Xie, C. Gu, & P. Wang, *Shiyou Huagong*, (2005) 34(2), 132-135 (abstract).

Fig. 1
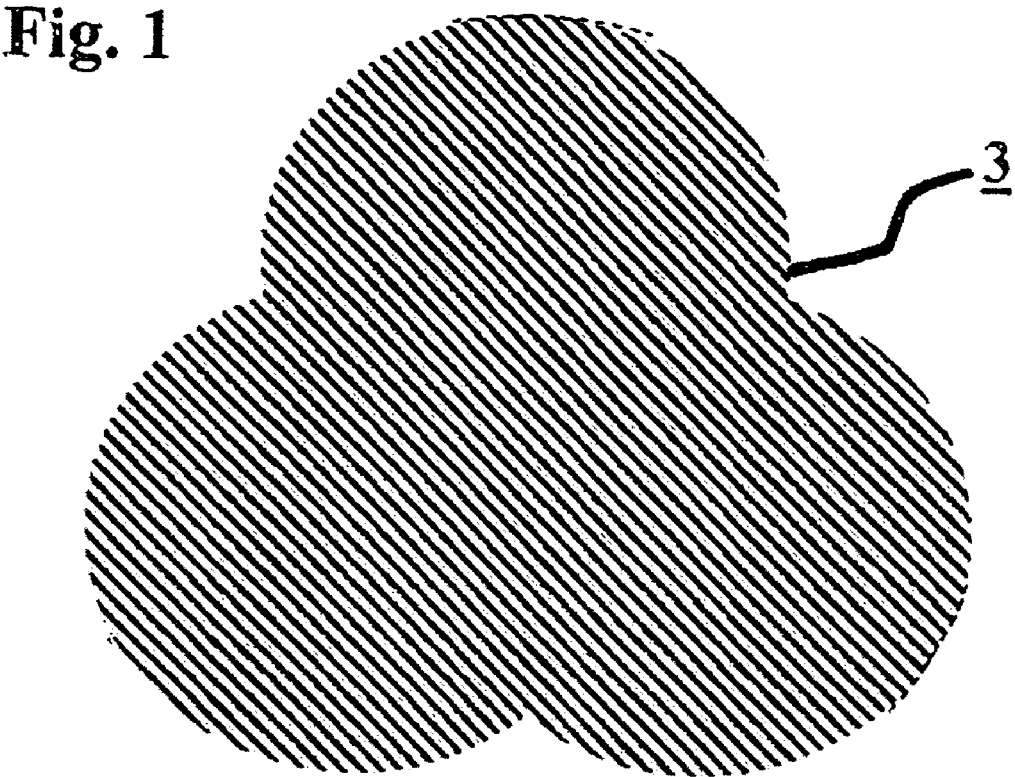
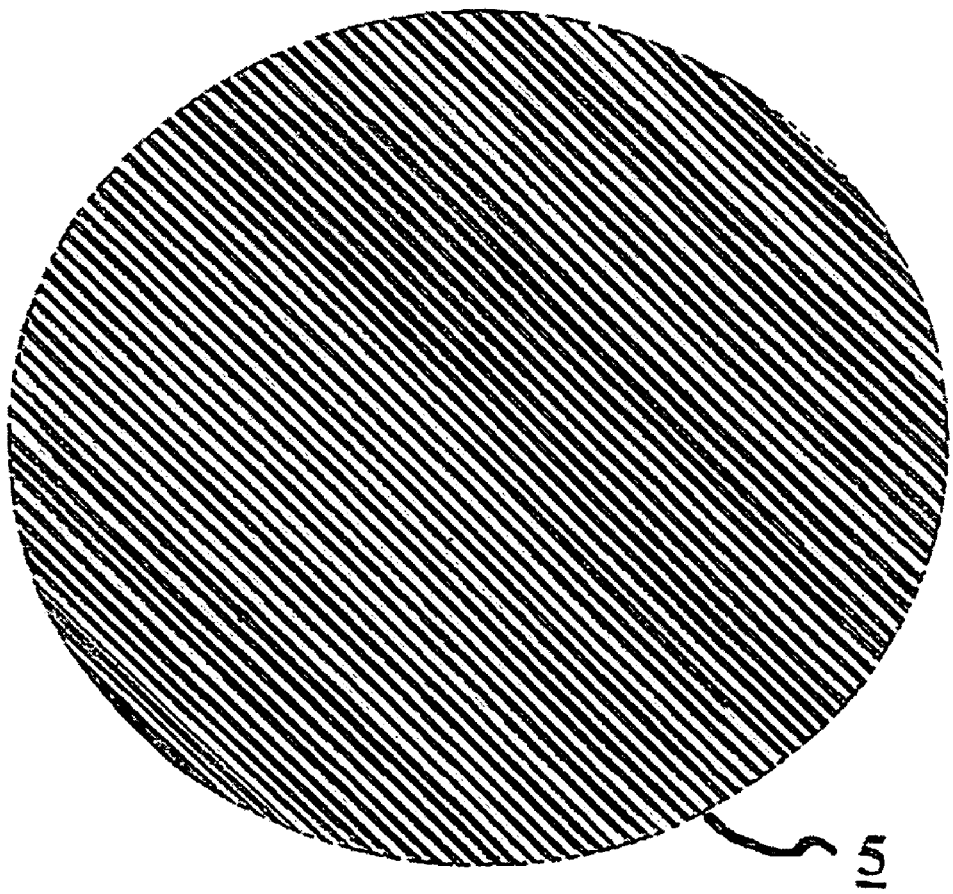

HYDROGENATION CATALYST AND HYDROGENATION METHOD

CROSS-REFERENCE TO RELATED APPLICATIONS

This application claims priority to U.S. Provisional Application 60/673,530 filed on Apr. 21, 2005, herein incorporated by reference in its entirety.

FIELD OF THE INVENTION

The present invention relates to a hydrogenation catalyst, a process for preparing the hydrogenation catalyst, and a process for hydrogenating aldehydes using the hydrogenation catalyst. More particularly, the present invention relates to a hydrogenation catalyst, its method of preparation, and its use in hydrogenating aldehydes, where the catalyst comprises an α-alumina support having nickel deposited on the support, and having ruthenium and a promoter deposited on the nickel and the α-alumina support, where the promoter is selected from the group consisting of rhenium, tungsten, molybdenum, chromium, lanthanum, tin, iron, silver, cobalt, copper, or mixtures thereof.

BACKGROUND OF THE INVENTION 1,3-propanediol (PDO) is a compound having multiple uses. It is used as a monomer unit in the production of polyesters and polyurethanes that are useful as films and as fibers for carpets and textiles. It is also useful as an engine coolant.

PDO may be prepared from ethylene oxide (EO) in a process involving two primary reactions. First, EO and synthesis gas ($H_2$/CO) are catalytically hydroformylated to 3-hydroxypropionaldehyde (HPA) in an organic solvent. The HPA is extracted from the solvent with water to form an aqueous solution of HPA, and the aqueous solution of HPA is then hydrogenated to form PDO.

The hydrogenation of HPA to PDO is performed using a hydrogenation catalyst. The hydrogenation catalyst should desirably have several features: 1) it should be highly active over an extended period of time; 2) it should cause the hydrogenation to be highly selective to the formation of PDO, rather than other compounds; 3) it should have a long catalyst life; 4) it should not be discharged into the PDO product stream; and 5) it should be economically cost effective, preferably using inexpensive components and, if required, as few expensive components as possible.

According to Hatch et al., U.S. Pat. No. 2,434,110, especially preferred catalysts for hydrogenating HPA to PDO are Raney nickel and Adkin's copper-chromium oxide. Hatch et al. also disclose that other suitable catalysts for hydrogenating HPA to PDO include catalytically active compounds of metals such as Fe, Co, Cu, Pd, Zr, Ti, Th, V, Ta, Ag, Mo, and Al. Slurry catalysts such as Raney nickel are known to have high activity and selectivity in converting HPA to PDO as a result of the homogeneous distribution of the catalyst in the hydrogenation reaction mixture.

Suspended or slurry catalysts, such as Raney nickel, however, are susceptible to being discharged into the PDO product stream in the form of soluble compounds, necessitating additional steps to purify the PDO product stream. Haas et al., U.S. Pat. No. 6,232,511, discloses that a supported ruthenium catalyst, wherein ruthenium is supported on an oxide phase, is useful in the hydrogenation of HPA to PDO, and avoids the problem of the metallic portion of the catalyst polluting the PDO product stream. Use of the supported ruthenium catalyst in a fixed-bed is preferred. Particularly preferred oxide phase supports are disclosed to be oxide phases that are resistant to acidic media such as titanium dioxide, silicon dioxide, aluminum silicate, zirconium dioxide, and zeolites. Aluminum oxide and magnesium oxide are disclosed as having lower acid resistance.

Supported, fixed-bed catalysts must have strong support materials in order to have a long catalyst life. Hydrogenation in a fixed trickle bed configuration is favored by small catalyst particle size. Reduction of the particle size, however, reduces the crush strength of the catalyst, which reduces the catalyst life. Catalysts having low crush strength collapse more readily over time and eventually plug the catalyst bed, at which point the catalyst must be changed.

Support materials having high crush strength are generally those that have less porosity, such as α-alumina. Supports that are less porous, however, have less surface to support the active catalyst metals, and, as a result, have less hydrogenation activity.

It is an object of the invention, therefore to provide a catalyst for the hydrogenation of HPA to PDO, wherein the catalyst is a supported catalyst that has relatively high crush strength, high activity over the life of the catalyst, long catalyst life, and that is economical and commercially attractive.

It is also an object of the present invention to provide a process for using such a catalyst to produce PDO from HPA in a hydrogenation reaction, where the reaction converts a high rate of HPA to PDO at a high degree of selectivity, and, where the process is continuous, the volume/time yield of PDO from HPA is high.

SUMMARY OF THE INVENTION

In one aspect, the present invention provides a hydrogenation catalyst effective for iron, cobalt, silver, copper or mixtures thereof; wherein the nickel contacts the support, and the ruthenium and the promoter at least partially overlay the nickel, and wherein the non-support metals comprise no more than 8 wt. % of the catalyst.

In another aspect, the present invention provides a process for hydrogenating aldehydes comprising: hydrogenating an aldehyde in the presence of a catalyst wherein the catalyst has a composition comprising a support comprising α-alumina and non-support metals comprising nickel, ruthenium, and a promoter selected from the group consisting of rhenium, tungsten, molybdenum, chromium, lanthanum, tin, or mixtures thereof; wherein the nickel contacts the support and the ruthenium and the promoter at least partially overlay the nickel. Preferably the aldehyde is a hydroxyaldehyde, and most preferably the aldehyde is 3-hydroxypropionaldehyde that is hydrogenated to 1,3-propanediol.

In a further aspect, the present invention provides a process for preparing a catalyst useful for hydrogenating an aldehyde comprising: a) depositing nickel on a support comprised of α-alumina; b) calcining the support with the nickel thereon; c) after calcining, depositing ruthenium and a promoter selected from the group consisting of rhenium, tungsten, molybdenum, chromium, lanthanum, tin, iron, cobalt, silver, copper, or mixtures thereof on the support and the nickel to form a catalyst precursor; and d) reducing the nickel, ruthenium, and promoter of the catalyst precursor to a metallic zero oxidation state to form the catalyst.

BRIEF DESCRIPTION THE DRAWINGS

FIG. 1 is a schematic representation of a tri-lobal catalyst pellet and a cylindrical catalyst pellet.

FIG. 2 is a graph showing the HPA hydrogenation catalytic activity for a series of sequential batch reactions of a catalyst of the present invention formed of an c-alumina support with 2.5 wt. % nickel deposited on the support, and 1 wt. % ruthenium and 1 wt. % rhenium deposited on the nickel and the support.

FIG. 3 is a graph showing the HPA hydrogenation catalytic activity for a series of sequential batch reactions of a catalyst of the present invention formed of an α-alumina support with 2.5 wt. % nickel deposited on the support, and 1 wt. % ruthenium and 1 wt. % rhenium deposited on the nickel and the support, where the catalyst was dried and exposed to air at ambient conditions prior to hydrogenation.

FIG. 4 is a graph showing the HPA hydrogenation catalytic activity for a series of sequential batch reactions of a catalyst of the present invention formed of an α-alumina support with 5.0 wt. % nickel deposited on the support, and 1 wt. % ruthenium and 1 wt. % rhenium deposited on the nickel and the support.

FIG. 5 is a graph showing the HPA hydrogenation catalytic activity for a series of sequential batch reactions of a catalyst of the present invention formed of an α-alumina support with 2.5 wt. % nickel and 1 wt. % molybdenum deposited on the support, and 1 wt. % ruthenium and 1 wt. % rhenium deposited on the nickel, molybdenum and the support.

DETAILED DESCRIPTION OF THE INVENTION

Figure 2:
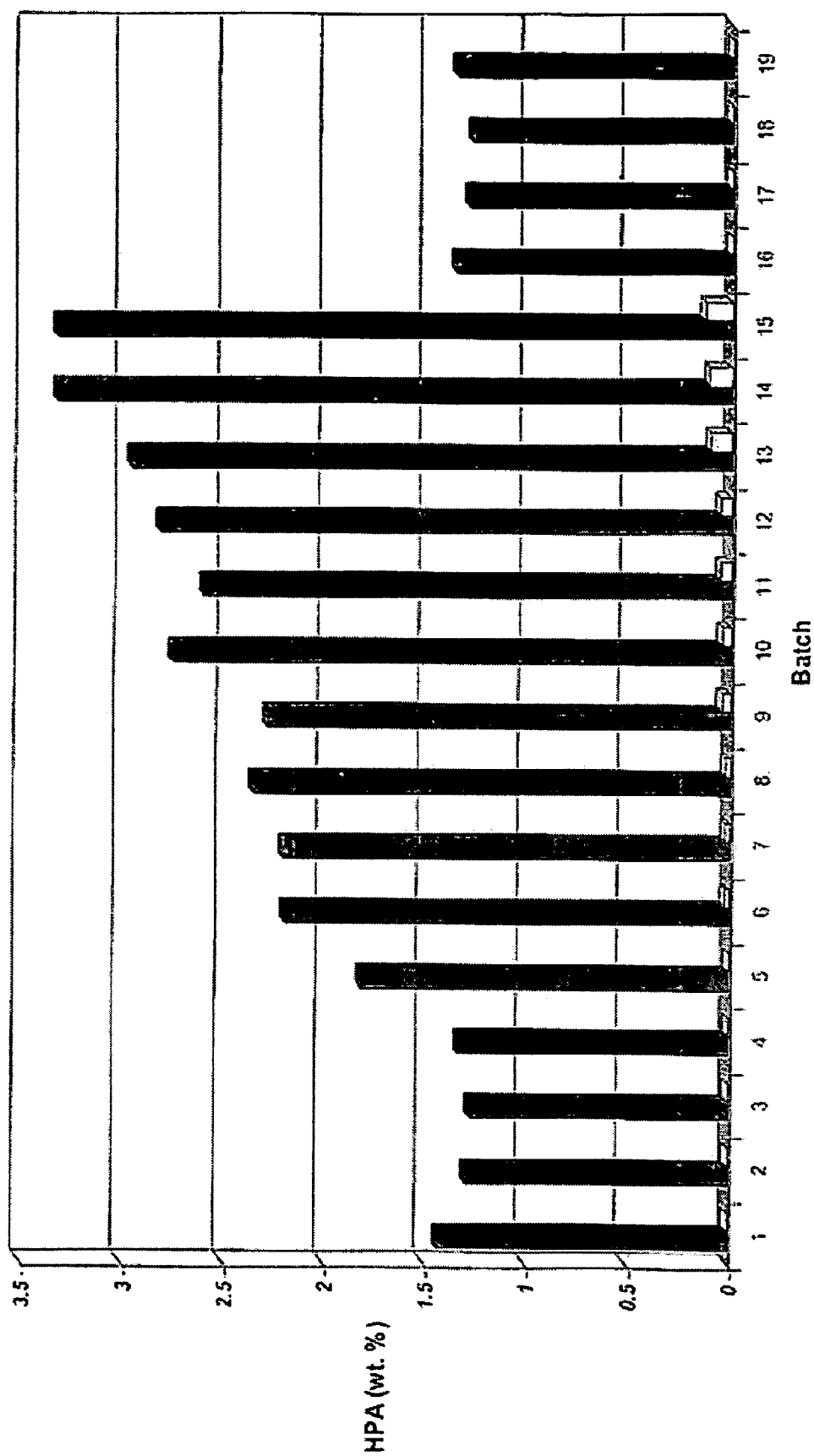

The present invention provides a hydrogenation catalyst, a method for its preparation, and a process for using the hydrogenation catalyst to hydrogenate aldehydes, particularly hydroxyaldehydes, and most particularly HPA to PDO. The catalyst is a supported catalyst that is particularly useful as a fixed-bed catalyst. The catalyst has an α-alumina support which provides excellent resistance against crushing and catalyst breakdown since α-alumina has a high crush strength. The catalyst comprises at least three non-support catalytically active metals-nickel that is deposited on the support, and ruthenium and a promoter metal that are deposited on the nickel and the support. The catalyst, with nickel as an underlayer and ruthenium and the promoter as at least a partial overlayer, displays surprisingly high hydrogenation catalytic activity over an extended period of time. As a result of the high activity of the catalyst metals as deposited on the support, a relatively small amount of each metal, compared to other HPA/PDO hydrogenation catalysts, may be utilized to effect the hydrogenation of HPA to PDO. The surprisingly high activity of the uniquely arranged catalyst metals enables the use of α-alumina as the support for the catalyst even though α-alumina can support only limited quantities of active metals. The α-alumina supported catalyst has a high crush strength and provides a long-lived fixed-bed catalyst. The catalyst of the present invention provides significant economic advantage over other HPA/PDO hydrogenation catalysts since relatively small amounts of catalytic metals are required, and the catalyst has a long life with high activity and a high degree of selectivity.

The Catalyst

The catalyst of the present invention comprises non-support catalytically active metals nickel, ruthenium, and a promoter selected from the group consisting of rhenium, tungsten, molybdenum, chromium, lanthanum, tin, iron, cobalt, silver, copper, and mixtures thereof; and a support comprising aluminum oxide ($Al_2O_3$) of the α-alumina phase. The support preferably comprises at least 92 wt.% of the catalyst, and more preferably comprises at least 94 wt. % of the catalyst. Most preferably, the support consists essentially of α-alumina.

The non-support metals comprise no more than 8 wt.% of the catalyst, preferably no more than 6 wt.% of the catalyst, and most preferably no more than 5 wt.% of the catalyst. The nickel comprises up to 6 wt. % of the catalyst, and more preferably comprises from 1.5 wt. % to 3.5 wt. % of the catalyst or from 1 wt. % to 3 wt % of the catalyst. The ruthenium comprises at least 0.1 wt. % of the catalyst, and more preferably comprises from 0.5 wt. % to 3.5 wt. % of the catalyst, and most preferably comprises from 0.75 wt. % to 1.5 wt. % of the catalyst. The promoter comprises at least 0.1 wt. % of the catalyst, and more preferably comprises from 0.5 wt. % to 3.5 wt. % of the catalyst, and most preferably comprises from 0.75 wt. % to 1.5 wt. % of the catalyst. Preferably the weight ratio, by metallic weight, of nickel to ruthenium plus promoter in the catalyst is from 1:2 to 6:1, and more preferably is from 1:1 to 3:1. Also, preferably, the weight ratio, by metallic weight, of ruthenium to the promoter is from 1:4 to 4:1. Most preferably the nickel comprises 2.5 wt. % of the catalyst, the ruthenium comprises 1 wt. % of the catalyst, and the promoter comprises 1 wt. % of the catalyst. In a most preferred embodiment, the promoter is rhenium.

The nickel is in contact with the support, and the ruthenium and promoter at least partially overlay the nickel. The nickel forms an underlayer deposited on the support and the ruthenium and promoter form an overlayer deposited, at least in part, on the nickel and may be deposited on the support. The combination of ruthenium and a promoter at least partially overlaying the nickel has unexpectedly been found to significantly increase the catalytic activity level of the catalyst in the hydrogenation of HPA to PDO over an extended period of time.

The support of the catalyst comprising α-alumina has a high degree of mechanical strength. The support may have few or no pores less than 500 Å in diameter, and a median pore diameter of from about 1400 to around 1800 Å, measured by mercury porosimetry at a 140° contact angle. The support preferably may have a pore volume (Hg) of from 0.35 ml/g to 0.45 ml/g. The lack of small pores provides the support with a relatively high crush strength, at least 2.26 kg/mm when the support has an average length of from 3 mm to 5 mm, and inhibits breakdown of the catalyst into fines or weakening of the support by chemical degradation over the life of the catalyst. The high crush strength of the support provides the catalyst with the strength necessary for a long catalyst life as a fixed-bed hydrogenation catalyst.

The crush strength is measured by a flat plate crush of individual catalyst pellets and reported as the average force required to crush the pellet when placed length-wise between two flat plates per average length of the catalyst pellet. The flat plate crush strength is calculated according to the following formula:

$$\frac{\text{Side Crush Strength}}{\text{per Length}} = \frac{\Sigma(\text{All Individual Crush Strength Measurements})}{\Sigma(\text{All Individual Length Measurements})}$$

The support of the catalyst contains little or no other forms of alumina other than α-alumina such as gamma-alumina, eta-alumina, delta-alumina, or theta-alumina. Other forms of alumina have substantially more porosity than α-alumina, and do not provide the desired mechanical strength and chemical resistance. In a preferred embodiment, the support of the catalyst contains no other forms of alumina as measured by powder X-ray diffraction than α-alumina. In a most preferred embodiment, the support of the catalyst consists essentially of α-alumina.

The support of the catalyst has a shape, size, and structure such that the support can be placed and retained in a fixed hydrogenation bed such as a trickle bed reactor. Most preferably, as shown in FIG. 1, the support is a tri-lobal 3 or cylindrical 5 pellet.

As a result of its limited porosity, the support may have an $N_2$ BET surface area of less than 10 $m^2/g$, and preferably has an $N_2$ BET surface area of from 3 $m^2/g$ to 9 $m^2/g$. Generally, decreasing support surface area increases the mechanical strength of the support while decreasing the available area upon which to deposit the active metal components of the catalyst. The support of the catalyst typically can retain no more than 8 wt. % of non-support metals relative to the combined weight of the α-alumina support and the non-support metals (the weight of the catalyst).

The hydrogenation catalyst of the present invention, however, has unexpectedly high hydrogenation activity despite the relative paucity of active metal components on the support. It is believed that the hydrogenation activity is due to the combination of "layering" the ruthenium and promoter metal components over the nickel component and support, and to the combination of the selected active metal components. As noted above, the nickel directly contacts the support and forms a non-support active metal "underlayer". The ruthenium and promoter metal are at least partially deposited on the nickel underlayer so that the ruthenium and the promoter act as an "overlayer". This "layering" has been found to provide the catalyst of the present invention with significantly more activity over time than a catalyst formed of the same active metal components that is not "layered".

It should be understood that the ruthenium and the promoter may be deposited both on the nickel and on the support, since the nickel may not form a complete coating over the support, and ruthenium and the promoter can be deposited either on the nickel or the support. It should also be understood that the ruthenium and the promoter may not be deposited so as to completely cover the nickel. As used herein the term "overlayer", therefore, should not be construed to mean that ruthenium and the promoter are necessarily deposited only on the nickel "underlayer" or that the ruthenium and the promoter entirely cover the nickel "underlayer". Rather, as used herein, the terms "overlayer" and "underlayer" should be construed to mean that the ruthenium and the promoter "overlayer" at least partially overlay the nickel "underlayer" and may contact the support.

The selected combination of non-support catalytically active metals of the catalyst also provides substantial hydrogenation activity over an extended period of time. The overlayer of ruthenium with a promoter metal provides a significant increase in hydrogenation activity, especially as the catalyst ages, relative to catalysts utilizing an overlayer of ruthenium alone or a promoter metal alone over a nickel underlayer, and relative to catalysts containing multiple or single metal components deposited as a single layer on a catalyst support.

The non-support active metals substantially increase the surface area of the finished catalyst relative to the surface area of the support, thereby providing more surface area than the support alone to catalytically interact to convert aldehydes in the presence of hydrogen. The surface area of the finished catalyst preferably is from 1.5 to 5 times the surface area of the support, and more preferably from 1.5 to 3 times the surface area of the support. The surface area of the finished catalyst typically will range from 10 $m^2/g$ to 25 $m^2/g$ as measured by $N_2$ adsorption, and will most typically range from 12 $m^2/g$ to 20 $m^2/g$.

The non-support metals decrease the pore volume and median pore diameter of the finished catalyst relative to the pore volume of the support. Typically the pore volume (Hg) of the finished catalyst will range from 0.2 cc/g to 0.35 cc/g, measured by mercury porosimetry at a 140° contact angle. Also, the median pore diameter of the finished catalyst will typically range from 1400 Å to 1700 Å.

The catalyst, in its activated state wherein the non-support metals are in their reduced metallic state, is surprisingly stable in air at ambient conditions. Preferably, the activated catalyst is stable indefinitely in air at temperatures from 10° C. to 30° C.

The catalyst has substantial catalytic activity to convert HPA under hydrogenation conditions, especially after an extended period of time. The catalyst has an initial activity sufficient to catalyze hydrogenation of HPA at a rate of at least 50 ml HPA/ml catalyst.hr at a temperature of from 50° C. to 100° C., a pH of from 4.0 to 6.5, and a hydrogen pressure of from 6.89 MPa to 10.68 MPa. Preferably the catalyst has an activity sufficient to catalyze hydrogenation of HPA at a rate of at least 25 ml HPA/ml catalyst.hr at a temperature of from 50° C. to 100° C., a pH of from 4.0 to 6.5, and a hydrogen pressure of from 6.89 MPa to 10.68 MPa after at least 24 hours exposure to the same HPA hydrogenation conditions. More preferably, the catalyst has an activity sufficient to catalyze hydrogenation of HPA at a rate of at least 35 ml HPA/ml catalyst.hr at a temperature of from 50° C. to 100° C., a pH of from 4.0 to 6.5, and a hydrogen pressure of from 6.89 MPa to 10.68 MPa after at least 24 hours of exposure to the same HPA hydrogenation conditions, and most preferably has an activity to catalyze hydrogenation of HPA at a rate of at least 40 ml HPA/ml catalyst.hr under such conditions after at least 24 hours of exposure to the same HPA hydrogenation conditions.

The catalyst also has a high crush strength, especially after an extended period of time of exposure to hydrogenation conditions. The catalyst, when having a length of from 3 mm to 5 mm and a diameter of from 0.8 mm to 1.2 mm, may have an initial crush strength of at least 2.26 kg/mm, and more preferably may have an initial crush strength of at least 2.72 kg/mm. The catalyst, when having a length of from 3 mm to 5 mm and a diameter of from 0.8 mm to 1.2 mm, further may have a crush strength of at least 2.04 kg/mm, and more preferably at least 2.26 kg/mm, after 79 days of exposure to HPA hydrogenation conditions-of a temperature of from 50° C. to 100° C.; a pH of from 4.0 to 6.5; and a hydrogen pressure of from 6.89 MPa to 10.68 MPa.

In another embodiment of the invention, the non-support metals of the catalyst may also include molybdenum mixed or alloyed with the nickel and deposited on the support as part of the "underlayer" of the catalyst. If present in the catalyst as a mixture or alloy with the nickel in the "underlayer" of the catalyst, the molybdenum is preferably present in the catalyst in a weight ratio, by metallic weight, relative to the nickel of from 1:1 to 1:20. The ruthenium and the promoter at least partially overlay the nickel and the molybdenum when molybdenum is included in the non-support metal underlayer with the nickel.

In a most preferred embodiment of the invention, the catalyst contains no halogens. Halogens may be deposited on the support of the catalyst in the preparation of the catalyst as a metal salt with the active metal components of the catalyst. Halogens, however, are known to corrode metal components of hydrogenation reactors, so it is desirable to avoid catalysts containing halogens. If metal salts are used to prepare the catalyst of the present invention, preferably the catalyst is prepared using metal salts of the active metals that are not halide salts.

Process for Preparing the Catalyst

The catalyst may be prepared by first preparing the support comprised of α-alumina; then depositing the nickel on the support; calcining the support with the nickel thereon; after calcining, depositing the ruthenium and promoter on the nickel and the support to form a catalyst precursor; and reducing the metals (nickel, ruthenium, and promoter) of the catalyst precursor to form the catalyst.

The α-alumina support may be prepared by calcining extruded alumina pellets. The extruded alumina pellets may be produced by mulling a mixture of pseudo-boehmite precipitated alumina powder with water and acid to form an extrudable mixture. The extrudable mixture may then be extruded through shaped dies to form the pellets, which may then be dried. The extruded pellets may then be calcined at a temperature of at least 1150° C., preferably from 1250° C. to 1350° C., for at least 2 hours to form the α-alumina phase support. The calcination reduces the pore volume ($H_2O$) of the alumina pellets from above 0.8 cc/g to 0.3-0.5 cc/g, and reduces the $N_2$ surface area of the pellets from above 225 $m^2/g$ to below 10 $m^2/g$ while increasing the median pore diameter of the pellets from about 100 Å to about 1400-1800 Å. Preferably the calcined α-alumina pellets used as the support have a tri-lobe 3 or cylindrical 5 shape, as shown in FIG. 1.

The nickel is deposited as a first layer, or underlayer, on the support comprised of α-alumina. The nickel should be dispersed relatively evenly over the surface of the support to ensure that the catalyst has high activity. The nickel may be deposited on the support by any procedure that deposits a desired quantity of nickel onto the support. The nickel is preferably deposited on the support by determining the water absorption capacity of the support, and loading the support in accordance with its water absorption capacity with an aqueous nickel solution that has a nickel content corresponding to the desired nickel concentration in the finished catalyst-where the entire quantity of the solution is absorbed by the support. The nickel solution is preferably prepared to provide a concentration of nickel, by metallic weight, of up to 6 wt. % of the finished catalyst, and more preferably from 1.5 wt % to 3.5 wt. % of the finished catalyst or from 1 wt. % to 3 wt. % of the finished catalyst. Most preferably, the nickel solution is prepared to provide a concentration of nickel, by metallic weight, of 2.5 wt. % of the finished catalyst.

Preferably, nickel carbonate is used in the aqueous nickel solution, although other water-soluble nickel compounds such as nickel nitrate or nickel acetate may be used either with nickel carbonate or in place of nickel carbonate in the aqueous nickel solution. Nickel halide salts may be used in the aqueous nickel solution, but are less preferred, since halides are known to be corrosive to steel components of hydrogenation reactors. Ammonium carbonate [$(NH_4)_2CO_3$] and ammonium hydroxide may be included in the aqueous nickel solution to aid in the dissolution of the nickel in the aqueous solution.

If desired, molybdenum may also be deposited on the support with the nickel as a mixture or alloy of nickel and molybdenum. The molybdenum, if included in the catalyst as a mixture or alloy with the nickel, is preferably included in a weight ratio relative to the nickel, by metallic weight, of from 1:1 to 1:20. Preferably, the desired amount of molybdenum is included in an aqueous base/water-soluble form in the aqueous nickel solution, which is then loaded onto the support. Preferably, molybdenum trioxide is used in the aqueous nickel/molybdenum solution, although other aqueous base/water soluble molybdenum compounds may be used such as ammonium dimolybdate and ammonium heptamolybdate tetrahydrate.

After the support is impregnated with the nickel, with or without molybdenum, the nickel-impregnated support may be aged. Preferably the support is aged at room temperature for a period of from 1 hour to 3 hours, most preferably for a period of 2 hours.

The nickel-impregnated support, with or without molybdenum, may be dried and calcined prior to being impregnated with ruthenium and the promoter. The nickel-impregnated support may be dried at a temperature of from 25° C. to 250° C. for a period of from 1 hour to 4 hours, and most preferably at a temperature of 150° C. for a period of 3 hours. After the nickel-impregnated support is dry, it may be calcined at a temperature of from 350° C. to 500° C. for a period of from 30 minutes to 2 hours, and most preferably at a temperature of 483° C. for a period of 1 hour.

Ruthenium and the promoter may then be deposited as a second layer, or overlayer, on the dried and calcined nickel-impregnated support. The ruthenium and the promoter should be dispersed relatively evenly over the nickel-impregnated support to ensure a high degree of catalytic activity. It should be understood that the ruthenium and the promoter may be deposited both on the nickel (and molybdenum, if present with the nickel) and the support, since the nickel may not form a complete coating over the support, and ruthenium and the promoter may be deposited either on the nickel or the support. The term "overlayer", therefore, should not be construed to mean that ruthenium and the promoter are necessarily deposited only on the nickel "underlayer".

The ruthenium and the promoter may be deposited on the nickel-impregnated support by any procedure that deposits a selected quantity of ruthenium and a second selected quantity of the promoter onto the support. Preferably the ruthenium and the promoter are deposited on the nickel-impregnated support by loading the nickel-impregnated support in accordance with its water absorption capacity with an aqueous solution containing ruthenium and a promoter in aqueous soluble forms. The aqueous solution of ruthenium and the promoter preferably have a ruthenium content and a promoter content corresponding to the desired quantity of the respective ruthenium and promoter metals on the finished catalyst when the entire quantity of the ruthenium/promoter solution is absorbed on the support.

The aqueous ruthenium/promoter solution is preferably prepared to provide a content of ruthenium, by metallic weight, of at least 0.1 wt. % of the finished catalyst, more preferably from 0.5 wt. % to 3.5 wt. % of the finished catalyst, and most preferably from 0.75 wt. % to 1.5 wt. % of the finished catalyst; and preferably to provide a content of promoter, by metallic weight, of at least 0.1 wt. % of the finished catalyst, more preferably from 0.5 wt. % to 3.5 wt. % of the finished catalyst, and most preferably from 0.75 wt. % to 1.5 wt. % of the finished catalyst. Preferably the aqueous solution of ruthenium/promoter is prepared to provide a weight ratio, by metallic weight, of nickel to ruthenium plus promoter in the finished catalyst of from 1:2 to 6:1, and more preferably of from 1:1 to 3:1. Also, preferably, the aqueous solution of ruthenium/promoter is prepared to provide a weight ratio, by metallic weight, of ruthenium to the promoter of from 1:4 to 4:1. Most preferably the ruthenium/promoter solution is prepared so the ruthenium comprises 1 wt. % of the finished catalyst and the promoter comprises 1 wt. % of the finished catalyst, especially where nickel has been deposited on the support in an amount that comprises 2.5 wt. % of the finished catalyst.

Preferably, ruthenium nitrosyl nitrate is used as the water-soluble ruthenium compound in the aqueous ruthenium/promoter solution. Other water-soluble ruthenium compounds such as ruthenium trichloride, potassium hexachlororuthenate, potassium tetraoxoruthenate, ruthenium tetraoxide, hexaammineruthenium trichloride, and potassium hexacyanoruthenate may be used either with ruthenium nitrosyl nitrate or in place of ruthenium nitrosyl nitrate in the aqueous ruthenium/promoter solution. Ruthenium halides are less preferred, however, since halides are known to be corrosive to steel components of hydrogenation reactors.

The promoter is preferably selected from a water-soluble compound of rhenium, tungsten, molybdenum, chromium, lanthanum, iron, cobalt, silver, copper, tin, or mixtures thereof. Most preferably, the promoter is selected from a water-soluble rhenium compound. A particularly preferred water-soluble rhenium compound is ammonium perrhenate ($NH_4ReO_4$).

After the nickel-impregnated support is impregnated with ruthenium and the promoter, the ruthenium/promoter/nickel-impregnated support may be aged. Preferably the support is aged at room temperature for a period of from 1 hour to 3 hours, most preferably for a period of 2 hours.

The ruthenium/promoter/nickel-impregnated support may then be dried to form the catalyst precurser. The ruthenium/promoter/nickel-impregnated support may be dried at a temperature of from 100° C. to 250° C. for a period of from 1 hour to 4 hours, and most preferably at a temperature of 150° C. for a period of 3 hours. The catalyst precursor contains the non-support metals at least one of which may be in their ionic, non-metallic states.

The catalyst precursor may then be activated to form the catalyst by reducing the non-support metals to their metallic, zero-oxidation states. The catalyst precursor may be reduced to form the catalyst by holding the catalyst precursor under a hydrogen atmosphere at an elevated temperature. Preferably the catalyst precursor is held at a temperature of from 100° C. to 500° C. for a period of from 20 minutes to 24 hours to reduce the non-support metals and activate the catalyst. The catalyst is preferably activated by heating the catalyst precursor under a flowing $H_2$ atmosphere. Most preferably, the catalyst is activated under flowing $H_2$ atmosphere by heating at a temperature ramped up from room temperature to 107° C. at 0.4° C. per minute, holding the catalyst precursor at 107° C. for 1 hour, ramping the temperature up from 107° C. to 288° C. at 0.9° C. per minute, holding the catalyst precursor at 288° C. for 4 hours, and cooling to room temperature.

The activated catalyst may be transferred to storage under an inert atmosphere and stored under liquid PDO prior to use. Surprisingly, however, the activated catalyst has been found to be stable in air under ambient conditions. The activated catalyst, therefore, may be loaded directly into a hydrogenation reactor, preferably in a fixed-bed, without being maintained under an inert atmosphere or stored in an inert liquid.

Process for Hydrogenating an Aldehyde

An aqueous solution of an aldehyde may be supplied to at least one hydrogenation reactor containing the catalyst of the invention, preferably in a fixed-bed configuration, for hydrogenation. The preferred activated catalyst is described above, where the catalyst comprises a support comprising α-alumina, and non-support metals comprising nickel, ruthenium, and a promoter selected from the group consisting of rhenium, tungsten, molybdenum, chromium, lanthanum, tin, iron, cobalt, silver, copper, or mixtures thereof, where the nickel contacts the support and the ruthenium and the promoter at least partially overlay the nickel. The preferred amounts and relative ranges of the support, nickel, ruthenium, and promoter are described above; and the preferred characteristics of the support are also described above. The method for preparing the catalyst is also described above. The catalyst preferably is formed in the shape of tri-lobal or cylindrical pellets. In one embodiment, the catalyst may contain molybdenum mixed or alloyed with nickel, as described above. In a most preferred embodiment, the promoter is rhenium.

The aldehyde to be hydrogenated may be any aldehyde that is at least partially soluble in water and is chemically stable in water. Preferably, the aldehyde is an aliphatic aldehyde, and more preferably the aldehyde is a relatively low molecular weight aliphatic aldehyde having from 3 to 12 carbon atoms. In one embodiment of the invention the aldehyde is a hydroxyaldehyde.

The aqueous solution of aldehyde may contain the aldehyde in a concentration in the range of 0.2 wt. % to 50 wt. %, based on the weight of the aqueous liquid, which is preferably water or water combined with the desired hydrogenation product. It is desirable to use a dilute solution of the aldehyde with a fixed-bed catalyst, preferably having an aldehyde concentration of at most 15 wt. %, more preferably having an aldehyde concentration of from 0.2 wt. % to 15 wt. %, and most preferably having an aldehyde concentration of at most 8 wt. %, particularly an aldehyde concentration of from 0.5 wt. % to 8 wt. %. Diffusion of $H_2$ through the fixed-bed catalyst pellet is the rate limiting step in hydrogenating the aldehyde, and the selectivity of hydrogenation of the aldehyde to the desired hydrogenation product is increased by utilizing an aqueous solution having a dilute concentration of aldehyde to ensure that the aldehyde is catalyzed in the presence of $H_2$ to form the desired product, rather than catalyzed to form undesirable side products in the absence of $H_2$.

Although any aqueous liquid that will not interfere with hydrogenation of the aldehyde, including water, can be used to dilute the aqueous solution of aldehyde to the desired concentration, it is preferred to employ an aqueous solution containing the desired hydrogenation product such as a portion of the product stream from the hydrogenation step. Dilution with such a product-containing solution serves to concentrate product in the system water, thus avoiding the high cost and recovery of dilute product from water which would result from the use of water alone as diluent.

The aldehyde in the dilute aqueous aldehyde solution is reacted with hydrogen in the presence of the catalyst using methods known in the art. A fixed-bed hydrogenation reactor is preferred for conducting the hydrogenation on an industrial scale with the catalyst of the invention. In such a reactor, the liquid reaction mixture flows or trickles over the catalyst in a fixed-bed together with the hydrogen. To ensure good distribution of the hydrogen in the reaction mixture and uniform distribution of the gas/liquid mixture over the entire cross-section of the fixed bed, the liquid reaction mixture and hydrogen may be passed together through static mixers before the catalyst bed.

The hydrogenation process can be carried out in one stage or in two or more sequential stages. Generally, the hydrogenation may be carried out at a temperature of from 30° C. to 190° C. and at a hydrogen pressure of from 3.44 MPa to 68.9 MPa. In a preferred embodiment, hydrogenation is initially carried out at a temperature of from 50° C. to 130° C. and a hydrogen pressure of from 8.96 MPa to 10.3 MPa, followed by a second stage hydrogenation carried out at a temperature higher than that of the first stage and within the range of from 70° C. to 155° C. and a hydrogen pressure of from 7.58 MPa to 10.3 MPa, and then optionally in a third stage hydrogenation at a temperature greater than the temperature of the second stage and with a temperature of 120° C. or greater, preferably from 120° C. to 190° C. and a hydrogen pressure of from 6.89 MPa to 10.3 MPa. Most preferably the initial hydrogenation is carried out at a temperature of less than 100° C. to increase the selectivity of the hydrogenation of the aldehyde to the desired product. The second hydrogenation stage and any subsequent hydrogenation stages can be carried out at higher temperatures without negatively affecting selectivity since most of the aldehyde is hydrogenated in the first stage, and the solution has a very dilute concentration of the aldehyde in the second and later hydrogenation stages. In this preferred process, the hydrogenation is optionally carried out in two or more separate hydrogenation vessels.

Process of Producing 1,3-Propanediol

Most preferably, HPA is the aldehyde to be hydrogenated to form PDO. PDO may be prepared by hydrogenating an aqueous solution of HPA in the presence of the catalyst of the present invention.

An aqueous solution of HPA can be prepared by a process involving the catalyzed hydroformylation (reaction with synthesis gas, $H_2/CO$) of ethylene oxide to form a dilute mixture of HPA in an organic solvent, typically methyl t-butyl ether (MTBE). The HPA in the organic solvent can be extracted into water to form a more concentrated HPA solution. U.S. Pat. No. 5,786,524, which is incorporated herein in its entirety by reference, describes such a process wherein ethylene oxide and synthesis gas are contacted at 50° C. to 100° C. and at 3.44 MPa to 34.4 MPa in the presence of a cobalt or rhodium catalyst and a catalyst promoter to produce a product mixture containing HPA. Water is added to the HPA mixture and most of the HPA is extracted into the water to provide an aqueous phase comprising a higher concentration of HPA and an organic phase containing at least a portion of the catalyst.

Alternatively, an aqueous solution of HPA can be prepared by hydration of acrolein, as described in detail in U.S. Pat. No. 5,015,789, which is incorporated herein in its entirety by reference. In that process, acrolein and water are reacted in a weight ratio of 1:2 to 1:20, preferably from 1:3 to 1:6, at 30° C. to 120° C., preferably at 50° C. to and a pressure in a range from 0.1 MPa to 2.0 MPa, preferably 0.2 MPa to 0.5 MPa, in the presence of an acidic cation exchanger resin to form HPA. After production of HPA, the HPA solution is separated from the ion exchanger, preferably by sedimentation or filtration, and the reaction mixture is separated from unreacted acrolein to provide a concentrated aqueous solution of HPA. The separation of acrolein may be carried out by distillation under reduced pressure, preferably in a thin-layer evaporator.

However obtained, the aqueous solution of HPA may be supplied to at least one hydrogenation reactor containing the activated catalyst, preferably in a fixed-bed configuration, for hydrogenation to PDO. The preferred activated catalyst is described above, where the catalyst comprises a support comprising α-alumina and non-support metals nickel, ruthenium and a promoter selected from rhenium, tungsten, molybdenum, chromium, lanthanum, tin, cobalt, iron, silver, copper or mixtures thereof, where the nickel contacts the support and the ruthenium and promoter at least partially overlay the nickel. The preferred amounts and relative ranges of the α-alumina support, nickel, ruthenium, and promoter are described above; and the preferred characteristics of the α-alumina support are also described above. The catalyst preferably is formed in the shape of tri-lobal or cylindrical pellets. In one embodiment, the catalyst may contain molybdenum mixed or alloyed with nickel, as described above. In a most preferred embodiment, the promoter is rhenium.

The aqueous solution of HPA should contain HPA in a concentration in the range of 0.2 wt. % to 50 wt. %, based on the weight of the aqueous liquid, which is usually water or a combination of water and PDO. It is desirable to use a dilute solution of HPA with a fixed-bed catalyst, preferably having an HPA concentration of at most 15 wt. % HPA, more preferably having an HPA concentration of from 0.2 wt. % to 15 wt. %, and most preferably having an HPA concentration of at most 8 wt. %, particularly an HPA concentration of from 0.5 wt. % to 8 wt. %. Diffusion of $H_2$ through the fixed-bed catalyst pellet is the rate limiting step in hydrogenating FPA to PDO, and the selectivity of hydrogenation of HPA to PDO is increased by utilizing an aqueous solution having a dilute concentration of HPA to ensure that HPA is catalyzed in the presence of $H_2$ to form PDO, rather than catalyzed to form undesirable side products in the absence of $H_2$.

Although any aqueous liquid that will not interfere with hydrogenation of HPA, including water, may be used to dilute the aqueous solution of HPA to the desired concentration, it is preferred to employ an aqueous PDO containing solution such as a portion of the product stream from the hydrogenation step. Dilution with such a PDO-containing solution serves to concentrate PDO in the system water, thus avoiding the high cost and recovery of dilute PDO from water which would result from the use of water alone as diluent.

The HPA in the dilute aqueous HPA solution may be reacted with hydrogen in the presence of the catalyst using methods known in the art. A fixed-bed hydrogenation reactor is preferred for conducting the hydrogenation on an industrial scale with the catalyst of the invention. In such a reactor, the liquid reaction mixture flows or trickles over the catalyst in a fixed-bed together with the hydrogen. To ensure good distribution of the hydrogen in the reaction mixture and uniform distribution of the gas/liquid mixture over the entire cross-section of the fixed bed, the liquid reaction mixture and hydrogen may be passed together through static mixers before the catalyst bed.

The hydrogenation process may be carried out in one stage or in two or more sequential stages. Generally, the hydrogenation may be carried out at a temperature of from 30° C. to 190° C. and at a hydrogen pressure of from 3.44 MPa to 68.9 MPa. In a preferred embodiment, hydrogenation is initially carried out at a temperature of from 50° C. to 130° C. and a hydrogen pressure of from 8.96 MPa to 10.3 MPa, followed by a second stage hydrogenation carried out at a temperature higher than that of the first stage and within the range of from 70° C. to 155° C. and a hydrogen pressure of from 7.56 MPa to 10.3 MPa, and then optionally in a third stage hydrogenation at a temperature greater than the temperature of the second stage and with a temperature of 120° C. or greater, preferably from 120° C. to 190° C. and a hydrogen pressure of from 6.89 MPa to 10.3 MPa. Most preferably the initial hydrogenation is carried out at a temperature of less than 100° C. to increase the selectivity of the hydrogenation of HPA to PDO. The second hydrogenation stage and any subsequent hydrogenation stages may be carried out at higher temperatures without negatively affecting selectivity since most of the HPA is hydrogenated in the first stage, and the solution has a very dilute concentration of HPA in the second and later hydrogenation stages. In this preferred process, the hydrogenation is optionally carried out in two or more separate hydrogenation vessels.

The hydrogenation reaction is preferably carried out at acidic conditions below pH 6.5 since LPA tends to form aldol condensation products and heavy end byproducts at higher pHs. Preferably the hydrogenation is carried out at a pH of from 4.0 to 6.5. Typically, an aqueous solution of HPA derived from a hydroformylation reaction of ethylene oxide and syngas contains 3-hydroxypropionic acid so that the aqueous solution of HPA is acidic. If desired, the pH of the HPA solution can be adjusted upwards with a base, preferably a hydroxide, or downwards with an acid, preferably a mineral acid, to the desired pH.

The hydrogenation reaction may be carried out in a batch process or in a continuous process. For industrial scale production of PDO from HPA it is preferred to utilize a continuous process.

The process of hydrogenating HPA to PDO of the present invention with the catalyst of the present invention provides a high degree and rate of conversion of HPA by hydrogenation, particularly over an extended period of time. HPA may be initially converted in the hydrogenation reaction at a rate of at least 50 ml HPA/ml catalyst.hr at a temperature of from 50° C. to 160° C., a pH of from 4.0 to 6.5, and a hydrogen pressure of from 6.89 MPa to 11.0 MPa. HPA may still be hydrogenated in the hydrogenation reaction with a high degree of activity after the catalyst is exposed to hydrogenation reaction conditions for an extended period of time. Preferably HPA is hydrogenated at a rate of at least 25 ml HPA/mi catalyst.hr at a temperature of from 50° C. to 160° C., a pH of from 4.0 to 6.5, and a hydrogen pressure of from 6.89 MPa to 11.0 MPa after at least 24 hours exposure to HPA hydrogenation conditions. More preferably, HPA is hydrogenated at a rate of at least 35 ml HPA/ml catalyst.hr at a temperature of from 50° C. to 160° C., a pH of from 4.0 to 6.5, and a hydrogen pressure of from 6.89 MPa to 11.0 MPa after at least 24 hours of exposure to HPA hydrogenation conditions, and most preferably HPA is hydrogenated at a rate of at least 40 ml HPA/ml catalyst.hr under such conditions after at least 24 hours of exposure to HPA hydrogenation conditions.

EXAMPLE 1

A catalyst according to the present invention was prepared comprising an α-alumina support, nickel, ruthenium, and rhenium, where the nickel is deposited on the α-alumina support and the ruthenium and rhenium are deposited on the nickel and on the α-alumina support. The catalyst was prepared such that the catalyst contained 2.5 wt. % nickel, 1 wt. % ruthenium, and 1 wt. % rhenium.

Gamma-alumina tri-lobe pellets were calcined at 1275° C. to prepare the α-alumina support. An aqueous nickel solution was prepared by dissolving 3.5 grams of ammonium carbonate in 15 ml of ammonium hydroxide solution (25%) with moderate heat and stirring, followed by the addition and dissolution of 6.8 grams of nickel carbonate in the ammonium carbonate/ammonium hydroxide solution. The solution volume was brought to 40 ml with additional ammonium hydroxide solution (25%). 100 grams of the α-alumina support was impregnated with the nickel solution, absorbing 100% of the solution volume. The nickel solution impregnated support was then aged for 2 hours at room temperature. The nickel-impregnated support was then dried at 150° C. for 3 hours, and then calcined at 453° C. for 1 hour in air.

An aqueous solution of ruthenium and rhenium was also prepared. 1.6 grams of ammonium perrhenate was dissolved in 10 ml of deionized water with low heat and stirring. 3.3 grams of ruthenium nitrosyl nitrate was then added and dissolved in the ammonium perrhenate solution with heating and stirring. The solution volume was then brought to 40 ml with deionized water. The calcined nickel-impregnated support was then impregnated with the total volume of the aqueous solution of ruthenium and rhenium, and aged for 1 hour at room temperature. The nickel/ruthenium-rhenium impregnated support was then dried at 200° C. for 2 hours in air to form the catalyst precursor.

The catalyst precursor was activated to form the catalyst by heating the catalyst precursor under flowing hydrogen. The catalyst precursor was heated to 107° C. by raising the temperature from ambient at 0.4° C./minute. The catalyst precursor was held at 107° C. for 1 hour, then the temperature was raised at 0.9° C./minute to 288° C. The catalyst precursor was held at 288° C. for 4 hours, and then was cooled to room temperature to provide the activated catalyst.

EXAMPLE 2

Hydrogenation of HPA to PDO was effected with a catalyst in accordance with the present invention having nickel deposited on an α-alumina support, and ruthenium and rhenium deposited on the nickel and the support. The catalyst contained 2.5 wt. % nickel, 1 wt. % ruthenium, and 1 wt. % rhenium.

The catalyst was prepared in accordance with the procedure described in Example 1, where the activated catalyst was maintained under liquid PDO after activation and prior to hydrogenation. A 21 ml volume of the catalyst, with a catalyst density of 0.70 g/cm³ and a void fraction of 0.42, was loaded into a batch hydrogenation wire basket to provide a catalyst charge of 14.7 grams, which was then topped with a ⅛" layer of inert denstone to prevent the catalyst from moving during the hydrogenation. The basket containing the catalyst was then secured in the cooling coils of a batch hydrogenation reactor. The catalyst was then rinsed three times with deionized nitrogen sparged water.

The catalyst was then subjected to 19 batch hydrogenation cycles, each cycle lasting for 120 minutes. Importantly, the catalyst was not renewed or refreshed between batches, so each batch sequentially aged the catalyst. After each batch cycle the hydrogenation reactor solution was drained through a dip tube then loaded with 300 ml of an aqueous HPA/PDO feed mixture containing 1% n-butanol internal standard by weight. The feed mixture of aqueous HPA/PDO for the 19 batch hydrogenation cycles in Example 2 was mixed as shown in Table 1 below.

TABLE 1

| | Cycle | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| HPA (ml) | 60 | 60 | 60 | 60 | 90 | 90 | 90 | 90 | 120 | 120 | 120 | 120 | 150 | 150 | 150 | 60 | 60 | 60 | 60 |
| PDO/ H₂O (ml) | 240 | 240 | 240 | 240 | 210 | 210 | 210 | 210 | 180 | 180 | 180 | 180 | 150 | 150 | 150 | 240 | 240 | 240 | 240 |
| Total (ml) | 300 | 300 | 300 | 300 | 300 | 300 | 300 | 300 | 300 | 300 | 300 | 300 | 300 | 300 | 300 | 300 | 300 | 300 | 300 |

The HPA content of the HPA portion of the feed mixture was between 5 wt. % and 15 wt. % prior to dilution with the PDO/H$_2$O solution.

The loaded reactor was pressured with hydrogen to 2.07 MPa and then vented slowly three times to remove air from the system. The vented, loaded reactor was then pressured to a range of 5.5 MPa to 6.2 MPa with hydrogen. The temperature of the pressurized loaded reactor was then raised to 60° C. After the temperature of the reactor was stable at 60° C., the hydrogen pressure was increased to the final hydrogenation reaction pressure of 7.17 MPa. The hydrogenation reaction was run for 120 minutes, and samples were taken of the reaction mixture at 0 minutes, 30 minutes, 60 minutes, and 120 minutes. The samples were analyzed by gas chromatograph for 3-hydroxypropionaldehyde and 1,3-propanediol in a solution of sample and tetrahydrofuran in a ratio, by volume, of sample to THF of 1:5. Kinetics were determined by the rate of disappearance of HPA.

The initial HPA content, final HPA content, and amount of HPA converted by the catalyst are shown in Table 2. Table 2 also shows the HPA conversion rate initially and the average HPA conversion rate for cycles 13-15 (catalyst activity after 24 hours of exposure to hydrogenation conditions, for hours 24-30). Finally, Table 2 shows the initial PDO content and the final PDO content.

TABLE 2

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1 | 1.43 | 0.00 | 4.28 | >50 | — | 18.82 | 21.35 |
| 2 | 1.29 | 0.00 | 3.87 | >50 | — | 18.91 | 21.95 |
| 3 | 1.27 | 0.00 | 3.82 | >50 | — | 19.61 | 21.48 |
| 4 | 1.33 | 0.00 | 3.98 | >50 | — | 19.68 | 22.36 |
| 5 | 1.82 | 0.00 | 5.47 | >50 | — | 16.86 | 20.59 |
| 6 | 2.20 | 0.02 | 6.55 | 61.9 | — | 17.32 | 21.06 |
| 7 | 2.21 | 0.02 | 6.58 | 60.1 | — | 18.11 | 20.47 |
| 8 | 2.36 | 0.02 | 7.02 | 60.2 | — | 18.72 | 23.49 |
| 9 | 2.29 | 0.04 | 6.76 | 56.5 | — | 16.09 | 20.40 |
| 10 | 2.76 | 0.04 | 8.15 | 58.5 | — | 16.39 | 21.18 |
| 11 | 2.61 | 0.05 | 7.68 | 56.5 | — | 15.88 | 19.92 |
| 12 | 2.83 | 0.05 | 8.35 | 55.9 | — | 17.12 | 21.70 |
| 13 | 2.97 | 0.10 | 8.61 | 51.7 | 50.3 | 14.38 | 19.30 |
| 14 | 3.33 | 0.11 | 9.66 | 50.8 | 50.3 | 13.96 | 19.39 |
| 15 | 3.33 | 0.13 | 9.62 | 48.2 | 50.3 | 13.89 | 20.17 |
| 16 | 1.36 | 0.00 | 4.07 | — | — | 18.73 | 20.21 |
| 17 | 1.30 | 0.00 | 3.89 | — | — | 19.41 | 22.23 |
| 18 | 1.28 | 0.00 | 3.83 | — | — | 19.43 | 21.98 |
| 19 | 1.36 | 0.00 | 4.08 | — | — | 21.38 | 24.29 |

FIG. 2 provides a graphical representation of the catalytic activity of the catalyst for hydrogenating HPA over time. The initial HPA concentration of the reaction mixture (as wt. %, shown as black bars, and the final HPA concentration of the reaction mixture (as wt. %, shown as white bars, are compared for each batch. As shown in FIG. 2, the catalyst is highly effective for converting HPA at a high activity rate over the entire set of batches.

The catalyst also showed good selectivity for producing PDO. The catalyst, under the hydrogenation conditions, converted HPA to PDO with at least at 100% selectivity, with the initial selectivity of 185% and 164% for batches 13-15, where selectivity is moles of PDO formed per moles of HPA consumed, expressed as a percent. Selectivity is greater than 100% due to conversions of other compounds to PDO.

of a batch hydrogenation reactor. The catalyst was then rinsed three times with deionized nitrogen sparged water.

The catalyst was then subjected to 19 batch hydrogenation cycles, each cycle lasting for 120 minutes, under the same conditions as used in Example 2 above, including the feed mixture of aqueous HPA/PDO.

The initial HPA content, final HPA content, and amount of HPA converted by the catalyst are shown in Table 3. Table 3 also shows the HPA conversion rate initially and the average HPA conversion rate for cycles 13-15 (catalyst activity after 24 hours of exposure to hydrogenation conditions, for hours 24-30 and ratio of 150:150 HPA/PDO feed). Finally, Table 3 shows the initial PDO content and the final PDO content.

TABLE 3

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1 | 1.18 | 0.00 | 3.55 | >50 | — | 18.91 | 21.73 |
| 2 | 1.19 | 0.00 | 3.57 | >50 | — | 19.56 | 21.90 |
| 3 | 1.09 | 0.00 | 3.28 | >50 | — | 19.18 | 21.31 |
| 4 | 1.16 | 0.00 | 3.48 | >50 | — | 20.27 | 22.24 |
| 5 | 1.91 | 0.00 | 5.72 | >50 | — | 17.48 | 20.82 |
| 6 | 1.83 | 0.00 | 5.50 | >50 | — | 16.87 | 20.67 |
| 7 | 1.92 | 0.00 | 5.76 | >50 | — | 17.18 | 20.61 |
| 8 | 2.02 | 0.00 | 6.06 | >50 | — | 18.32 | 22.11 |
| 9 | 2.80 | 0.00 | 8.39 | >50 | — | 15.75 | 20.34 |
| 10 | 2.85 | 0.04 | 8.42 | 56.2 | — | 15.34 | 19.63 |
| 11 | 2.73 | 0.04 | 8.06 | 55.8 | — | 15.34 | 19.70 |
| 12 | 2.90 | 0.04 | 8.58 | 62.0 | — | 16.08 | 20.59 |
| 13 | 3.47 | 0.11 | 10.07 | 49.3 | 48.0 | 13.20 | 18.53 |
| 14 | 3.66 | 0.11 | 10.58 | 47.0 | 48.0 | 13.32 | 18.42 |
| 15 | 3.95 | 0.13 | 11.47 | 48.0 | 48.0 | 13.13 | 18.39 |
| 16 | 1.32 | 0.00 | 3.95 | — | — | 18.88 | 21.12 |
| 17 | 1.26 | 0.00 | 3.78 | — | — | 19.39 | 20.86 |
| 18 | 1.19 | 0.00 | 3.58 | — | — | 19.52 | 21.75 |
| 19 | 1.31 | 0.00 | 3.92 | — | — | 20.58 | 22.50 |

EXAMPLE 3

Hydrogenation of HPA to PDO was effected with a catalyst of the present invention having nickel deposited on an α-alumina support, and ruthenium and rhenium deposited on the nickel and the support, where the catalyst had been dried and exposed to air under ambient conditions prior to hydrogenation. The catalyst contained 2.5 wt. % nickel, 1 wt. % ruthenium, and 1 wt. % rhenium.

Figure 3:
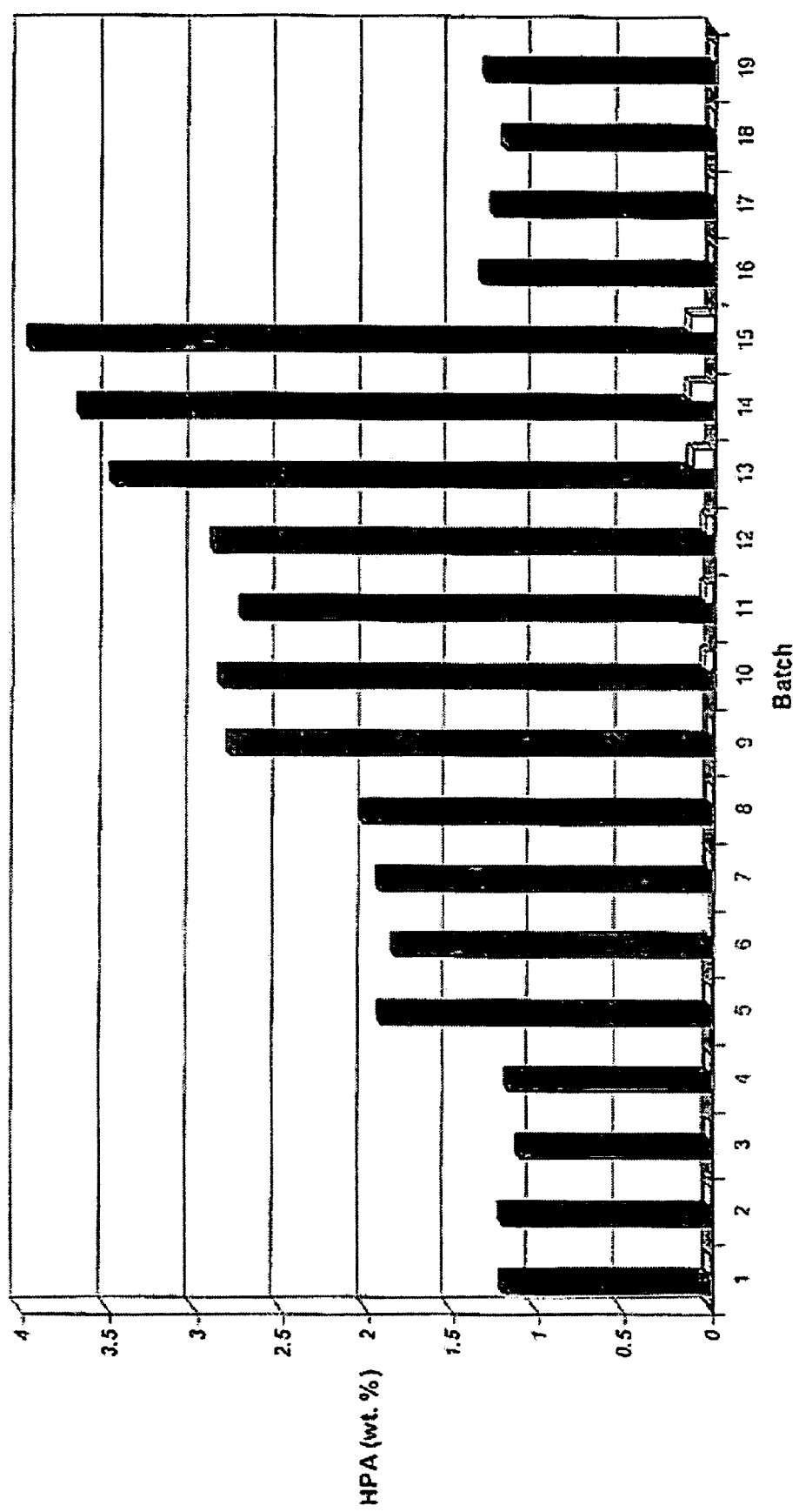

The catalyst was prepared in the same manner as the catalyst in Example 1, except the activated catalyst was exposed to air at ambient conditions prior to being loaded into a hydrogenator. A 21 ml volume of the activated catalyst with a catalyst density of 0.94 g/cm$^3$ and a void fraction of 0.42 was loaded dry into a batch hydrogenation wire basket to provide a catalyst charge of 19.7 grams, which was then topped with a ⅛" layer of inert denstone to prevent the catalyst from moving during the hydrogenation. The basket containing the catalyst was then secured in the cooling coils FIG. 3 provides a graphical representation of the catalytic activity of the catalyst for hydrogenating HPA over time. The initial HPA concentration of the reaction mixture (as wt. %), shown as black bars, and the final HPA concentration of the reaction mixture (as wt. %), shown as white bars, are compared for each batch. As shown in FIG. 3, the catalyst is highly effective for converting HPA at a high activity rate over the entire set of batches.

The catalyst also showed good selectivity for producing PDO. The catalyst, under the hydrogenation conditions, converted HPA to PDO with at least 100% selectivity, with the initial selectivity of 195% and 143% for batches 13-15, where selectivity is moles of PDO formed per moles of HPA consumed, expressed as a percent. Selectivity is greater than 100% due to conversions of other compounds to PDO.

EXAMPLE 4

Hydrogenation of HPA to PDO was effected with a catalyst of the present invention having nickel deposited on an α-alumina support, and ruthenium and rhenium deposited on the nickel and the support. The catalyst contained a higher level of nickel than that of Examples 1-3. In particular the catalyst contained 5.0 wt. % nickel, 1 wt. % ruthenium, and 1 wt. % rhenium.

The catalyst was prepared in the same manner as Example 1, except 1) 50 grams of α-alumina support was impregnated with 20 ml of a solution containing 6.75 grams of nickel carbonate and 3.5 grams of ammonium carbonate in an ammonium hydroxide solution (25%); and 2) the calcined nickel-impregnated support was impregnated with 20 ml of an aqueous solution containing 0.8 grams of ammonium perrhenate and 1.5 grams of ruthenium trichloride in deionized water. The activated catalyst was maintained under PDO until hydrogenation. The hydrogenation was conducted in the same manner as set forth in Example 2.

The initial HPA content, final HPA content, and amount of HPA converted by the catalyst are shown in Table 4. Table 4 also shows the HPA conversion rate initially and the average HPA conversion rate for cycles 13-15 (catalyst activity after 24 hours of exposure to hydrogenation conditions, for hours 24-30). Finally, Table 4 shows the initial PDO content and the final PDO content.

EXAMPLE 5

Hydrogenation of HPA to PDO was effected with a catalyst of the present invention having nickel and molybdenum deposited on an α-alumina support, and ruthenium and rhenium deposited on the nickel/molybdenum. The catalyst contained 2.5 wt. % nickel, 1 wt. % molybdenum, 1 wt. % ruthenium, and 1 wt. % rhenium.

The catalyst was prepared as in Example 1 except 1) 50 grams of α-alumina support was impregnated with 20 ml of a solution containing 3.34 grams of nickel carbonate, 0.81 grams of molybdenum trioxide ($MoO_3$), and 1.74 grams of ammonium carbonate in an ammonium hydroxide solution (25%) which was then dried and calcined as in Example 1; and the calcined nickel/molybdenum-impregnated support was impregnated with 20 ml of a solution containing 1.4 grams of ruthenium trichloride ($RuCl_3$) and 0.8 grams of ammonium perrhenate in deionized water. The activated catalyst was maintained under PDO until hydrogenation. The hydrogenation was conducted in the same manner as set forth in Example 2, except the catalyst had a catalyst density

TABLE 4

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1 | — | 0.00 | 6.59 | >50 | — | 18.00 | 19.09 |
| 2 | — | 0.00 | 6.28 | >50 | — | 18.14 | 20.10 |
| 3 | — | 0.00 | 5.87 | >50 | — | 16.72 | 21.16 |
| 4 | — | 0.00 | 6.57 | >50 | — | 19.70 | 21.15 |
| 5 | 1.82 | 0.02 | 13.84 | 58.3 | — | 18.05 | 21.75 |
| 6 | 2.23 | 0.02 | 16.51 | 60.3 | — | 18.51 | 20.63 |
| 7 | 2.25 | 0.02 | 16.23 | 61.2 | — | 17.58 | 22.28 |
| 8 | 2.24 | 0.02 | 16.94 | 62.6 | — | 18.56 | 21.63 |
| 9 | 2.27 | 0.06 | 14.91 | 55.5 | — | 15.39 | 19.52 |
| 10 | 2.80 | 0.07 | 16.05 | 50.9 | — | 15.66 | 19.63 |
| 11 | 3.00 | 0.08 | 15.83 | 51.3 | — | 16.63 | 19.75 |
| 12 | 2.88 | 0.09 | 17.45 | 47.8 | — | 15.92 | 20.98 |
| 13 | 3.10 | 0.21 | 12.85 | 41.4 | 37.5 | 13.68 | 19.53 |
| 14 | 3.74 | 0.31 | 15.51 | 34.8 | 37.5 | 13.65 | 21.16 |
| 15 | 4.05 | 0.28 | 15.67 | 36.3 | 37.5 | 14.99 | 18.99 |
| 16 | 1.27 | 0.01 | 16.72 | 54.9 | — | 20.44 | 25.34 |
| 17 | 1.26 | 0.01 | 6.60 | 76.3 | — | 20.62 | 23.55 |
| 18 | 1.26 | 0.01 | 6.34 | 74.2 | — | 21.32 | 25.27 |
| 19 | 1.14 | 0.01 | 6.61 | 60.0 | — | 18.81 | 21.61 |

Figure 4:
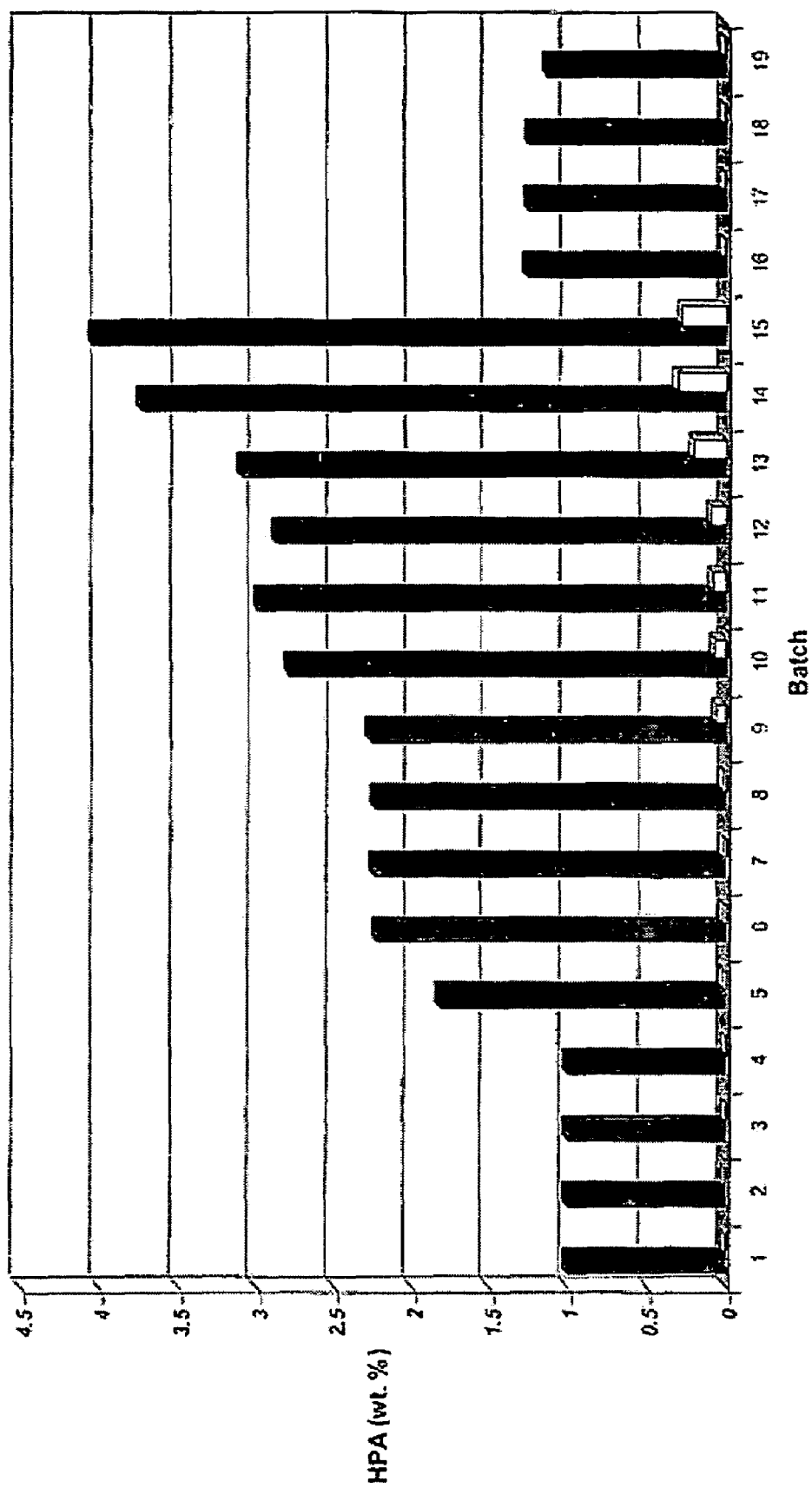

FIG. 4 provides a graphical representation of the catalytic activity of the catalyst for hydrogenating HPA over time. The initial HPA concentration of the reaction mixture (as wt. %), shown as black bars, and the final HPA concentration of the reaction mixture (as wt. %), shown as white bars, are compared for each batch. As shown in FIG. 4, the catalyst with 5% nickel deposited on an α-alumina support with 1 wt. % ruthenium and 1 wt. % rhenium deposited on the nickel and the support is effective for converting HPA at a high activity rate over the entire set of batches. It should be noted, however, that comparable rates of activity can be achieved by utilizing less nickel as shown in Examples 2-3 above, therefore, from a commercial standpoint, it is preferable to use less nickel.

of 0.58 g/cm³ and a void fraction of 0.42, and the 21 ml volume of catalyst provided a catalyst charge of 12.2 grams. The catalyst batch sequence was 4 cycles at 60:240 HPA:PDO, 12 cycles at 150:150, followed by 4 cycles at 60:240. Cycles 13-15 as in previous examples were at a 150:150 ratio.

The initial HPA content, final HPA content, and amount of HPA converted by the catalyst are shown in Table 5. Table 5 also shows the HPA conversion rate initially and the average HPA conversion rate for cycles 13-15 (catalyst activity after 24 hours of exposure to hydrogenation conditions, for hours 24-30). Finally, Table 5 shows the initial PDO content and the final PDO content.

TABLE 5

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1 | 2.20 | 0.00 | 6.59 | >50 | — | 16.65 | 19.84 |
| 2 | 2.09 | 0.00 | 6.28 | >50 | — | 17.42 | 20.06 |
| 3 | 1.96 | 0.00 | 5.87 | >50 | — | 17.12 | 20.44 |
| 4 | 2.19 | 0.00 | 6.57 | >50 | — | 18.76 | 21.32 |
| 5 | 4.74 | 0.13 | 13.84 | 55.4 | — | 12.31 | 19.38 |
| 6 | 5.71 | 0.20 | 16.51 | 48.3 | — | 12.46 | 19.85 |
| 7 | 5.70 | 0.29 | 16.23 | 43.9 | — | 13.16 | 19.60 |
| 8 | 5.97 | 0.32 | 16.94 | 42.8 | — | 13.26 | 20.29 |
| 9 | 5.32 | 0.35 | 14.91 | 41.2 | — | 12.37 | 19.13 |
| 10 | 5.75 | 0.40 | 16.05 | 38.2 | — | 12.72 | 20.32 |
| 11 | 5.73 | 0.45 | 15.83 | 36.8 | — | 12.68 | 20.50 |
| 12 | 6.38 | 0.57 | 17.45 | 34.8 | — | 14.08 | 21.61 |
| 13 | 4.58 | 0.30 | 12.85 | 43.5 | 40.1 | 12.56 | 19.81 |
| 14 | 5.57 | 0.40 | 15.51 | 38.3 | 40.1 | 12.38 | 19.51 |
| 15 | 5.63 | 0.40 | 15.67 | 38.6 | 40.1 | 12.53 | 20.21 |
| 16 | 6.03 | 0.46 | 16.72 | 37.6 | — | 13.56 | 20.62 |
| 17 | 2.20 | 0.00 | 6.60 | — | — | 18.60 | 21.54 |
| 18 | 2.11 | 0.00 | 6.34 | — | — | 18.43 | 21.63 |
| 19 | 2.20 | 0.00 | 6.61 | — | — | 19.30 | 22.05 |

Figure 5:
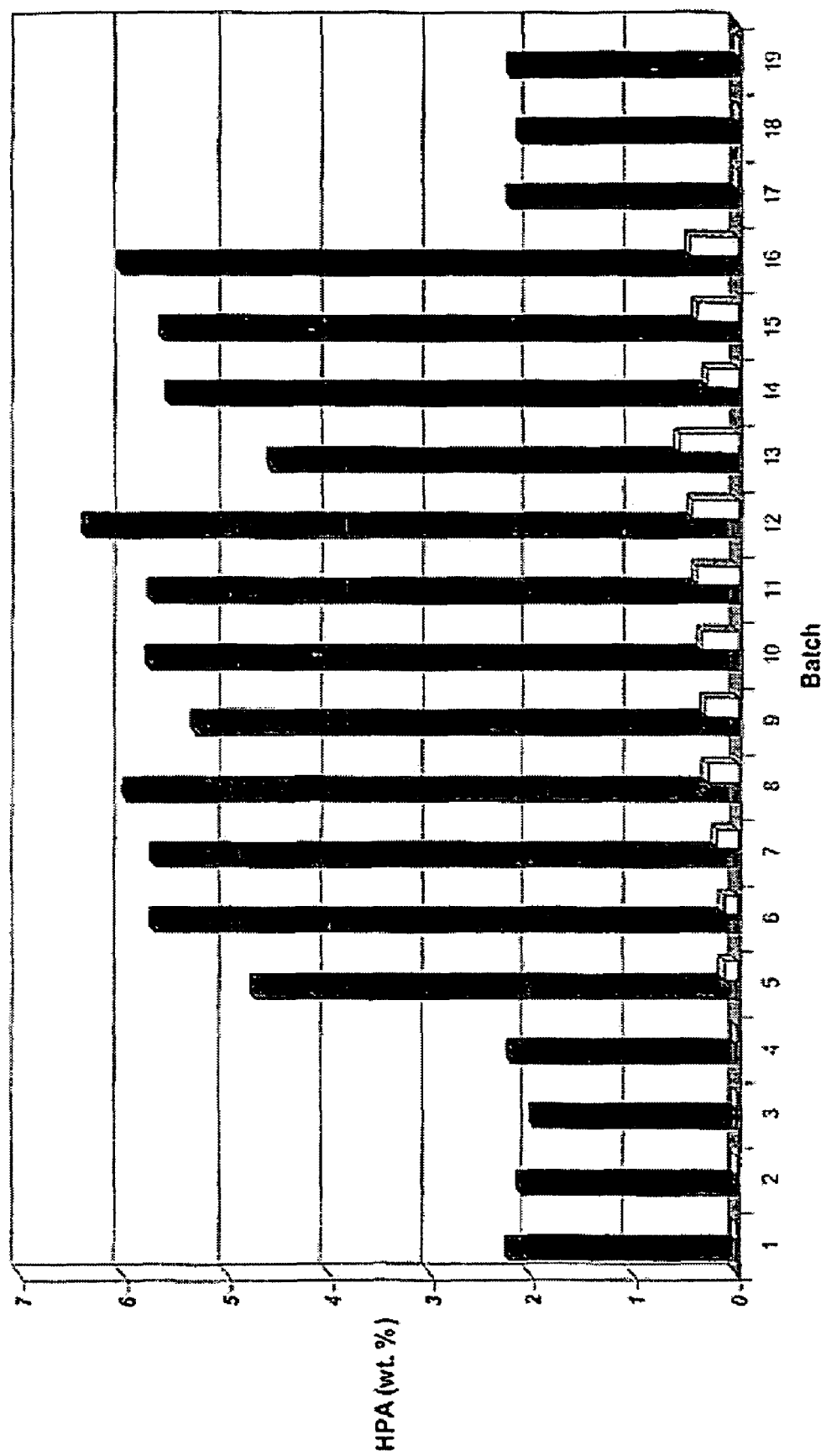

FIG. 5 provides a graphical representation of the catalytic activity of the catalyst for hydrogenating HPA over time. The initial HPA concentration of the reaction mixture (as wt. %), shown as black bars, and the final HPA concentration of the reaction mixture (as wt. %), shown as white bars, are compared for each batch. As shown in FIG. 5, the catalyst with molybdenum mixed with nickel is effective for converting HPA at a high activity rate over the entire set of batches.

The catalyst also showed good selectivity for producing PDO. The catalyst, under the hydrogenation conditions, converted HPA to PDO with at least 100% selectivity, with the initial selectivity of 136% and 147% for batches 13-15, where selectivity is moles of PDO formed per moles of HPA consumed, expressed as a percent. Selectivity is greater than 100% due to conversions of other compounds to PDO.

EXAMPLE 6

Hydrogenation of HPA to PDO using a catalyst not of the present invention that was prepared by impregnating an α-alumina support with nickel, ruthenium, and rhenium in a single step was conducted for comparative purposes. The catalyst contained 2.5 wt. % nickel, 1.0 wt. % ruthenium, and 1.0 wt. % rhenium.

Gamma-alumina tri-lobe pellets were calcined at 1275° C. to prepare the α-alumina support. An aqueous solution was prepared by dissolving 6.4 grams of nickel nitrate (Ni(NO$_3$)$_2$), 0.75 grams of ammonium perrhenate (NE$_4$ReO$_4$), and 1.65 grams of ruthenium nitrosyl nitrate (Ru(NO)(NO$_3$)$_2$) in deionized water to a total volume of 20 ml. 50 grams of the α-alumina support was impregnated with the total volume of the solution, and the impregnated support was aged for 1 hour. The nickel/ruthenium/rhenium impregnated support was then calcined for 1 hour at 482° C. (900° F.) to form a catalyst precursor.

The catalyst precursor was activated by heating the catalyst precursor under flowing hydrogen. The catalyst precursor was heated to 107° C. by raising the temperature from ambient at 0.4° C./minute. The catalyst precursor was held at 107° C. for 1 hour, then the temperature was raised at 0.9° C./minute to 288° C. The catalyst precursor was held at 288° C. for 4 hours, and then was cooled to room temperature to provide the activated catalyst. The activated catalyst was maintained under PDO until hydrogenation.

A 21 ml volume of the activated catalyst having a catalyst density of 0.60 g/cm$^3$ and a void fraction of 0.42 was loaded into a batch hydrogenation wire basket to provide a catalyst charge of 12.5 grams, which was then topped with a ⅛" layer of inert denstone to prevent the catalyst from moving during hydrogenation. The basket containing the catalyst was then secured in the cooling coils of a batch hydrogenation reactor. The catalyst was then rinsed three times with deionized nitrogen sparged water.

The catalyst was then subjected to 19 batch hydrogenation cycles, each cycle lasting 120 minutes. Importantly, the catalyst was not renewed or refreshed between batches, so each batch sequentially aged the catalyst. After each batch cycle the hydrogenation reactor was drained then loaded with 300 ml of an aqueous HPA/PDO feed mixture containing 1% n-butanol by weight. The feed mixture of aqueous HPA/PDO for the 19 batch hydrogenation cycles was mixed as shown in Table 1 above. The HPA content of the HPA feed was the same as described above with respect to Table 1 above. The hydrogenation was then conducted as described in Example 2 above.

The initial HPA content, final HPA content, and amount of HPA converted by the catalyst are shown in Table 6. Table 6 also shows the HPA conversion rate initially and the average HPA conversion rate for cycles 13-15 (catalyst activity after 24 hours of exposure to hydrogenation conditions, for hours 24-30). Finally, Table 6 shows the initial PDO content and the final PDO content.

TABLE 6

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1  | 0.39 | 0.00 | 1.18 | >50  | —   | 22.06 | 22.21 |
| 2  | 1.50 | 0.00 | 4.49 | >50  | —   | 20.08 | 22.08 |
| 3  | 1.32 | 0.00 | 3.97 | >50  | —   | 19.68 | 22.16 |
| 4  | 1.30 | 0.03 | 3.81 | >50  | —   | 19.81 | 22.18 |
| 5  | 1.83 | 0.26 | 4.72 | 26.7 | —   | 17.35 | 20.49 |
| 6  | 1.92 | 0.31 | 4.85 | 24.9 | —   | 17.18 | 19.93 |
| 7  | 1.86 | 0.32 | 4.61 | 24.1 | —   | 16.79 | 19.59 |
| 8  | 1.95 | 0.36 | 4.79 | 22.8 | —   | 17.49 | 20.40 |
| 9  | 2.86 | 1.04 | 5.46 | 14.1 | —   | 16.58 | 19.93 |
| 10 | 2.97 | 1.25 | 5.17 | 11.9 | —   | 16.31 | 19.52 |
| 11 | 2.93 | 1.32 | 4.83 | 9.8  | —   | 16.59 | 19.41 |
| 12 | 2.84 | 1.41 | 4.30 | 4.9  | —   | 17.05 | 19.45 |
| 13 | 2.98 | 2.29 | 2.05 | 5.1  | 5.3 | 14.97 | 17.56 |
| 14 | 3.56 | 2.34 | 3.68 | 5.9  | 5.3 | 14.57 | 16.62 |
| 15 | 3.53 | 2.30 | 3.70 | 12.6 | 5.3 | 14.29 | 17.05 |
| 16 | 1.45 | 0.57 | 2.64 | 16.5 | —   | 19.48 | 21.37 |
| 17 | 1.33 | 0.37 | 2.87 | 17.8 | —   | 20.97 | 21.58 |
| 18 | 1.25 | 0.32 | 2.78 | 20.5 | —   | 20.29 | 21.98 |
| 19 | 1.22 | 0.27 | 2.82 | —    | —   | 20.22 | 23.49 |

Figure 6:
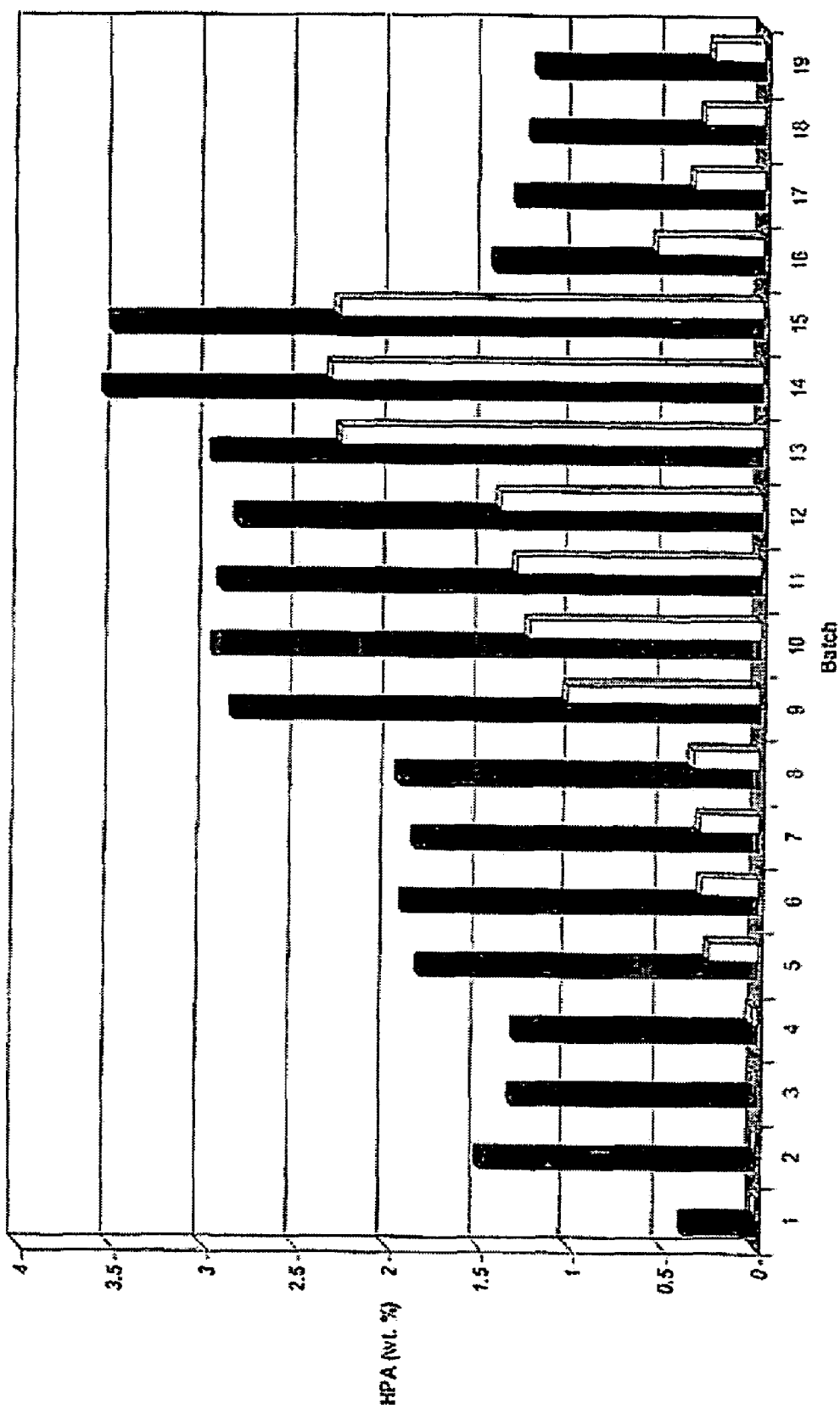
FIG. 6 is a graph showing the HPA hydrogenation catalytic activity for a series of sequential batch reactions of a catalyst not of the present invention formed of an α-alumina support with 2.5 wt. % nickel, 1 wt. % ruthenium, and 1 wt. % rhenium deposited on the support.

FIG. 6 provides a graphical representation of the catalytic activity of the catalyst for hydrogenating HPA over time. The initial HPA concentration of the reaction mixture (as wt. %), shown as black bars, and the final HPA concentration of the reaction mixture (as wt. %), shown as white bars, are compared for each batch. As shown in FIG. 6, particularly compared with FIGS. 2-5, the catalyst having nickel, ruthenium, and rhenium deposited on an α-alumina support in a single impregnation was not as effective in converting HPA over the entire set of batches as the catalysts prepared according to the present invention where nickel was deposited on an α-alumina support first, and then ruthenium and rhenium were deposited on the nickel and the support.

EXAMPLE 7

For comparative purposes, hydrogenation of HIPA to PDO was effected with a catalyst not of the present invention having nickel deposited on an α-alumina support, and ruthenium deposited on the nickel and the support in a second impregnation. The catalyst contained 2.5 wt. % nickel, and 1 wt. % ruthenium but contained no promoter.

Gamma-alumina tri-lobe pellets were calcined at 1275° C. to prepare the dry α-alumina support. An aqueous nickel solution was prepared by dissolving 1.7 grams of ammonium carbonate and 3.4 grams of nickel carbonate in an ammonium hydroxide solution (25%) to a total volume of 20 ml with moderate heat and stirring. 50 grams of the α-alumina support was impregnated with the nickel solution, absorbing 100% of the solution volume. The nickel solution impregnated support was then aged for 1 hour. The nickel-impregnated support was then dried at 150° C. for 3 hours, and then calcined at 453° C. for 1 hour in air.

An aqueous solution of ruthenium was also prepared. 1.5 grams of ruthenium trichloride (RuCl$_3$*3H$_2$O) was dissolved in deionized water to a total volume of 20 ml with heating and stirring. The calcined nickel-impregnated support was then impregnated with all of the aqueous solution of ruthenium, and aged at room temperature for 1 hour. The nickel/ruthenium-impregnated support was then dried at 200° C. for 2 hours in air to form the catalyst precursor.

The catalyst precursor was activated by heating the catalyst precursor under flowing hydrogen. The catalyst precursor was heated to 107° C. by raising the temperature from ambient at 0.4° C./minute. The catalyst precursor was held at 107° C. for 1 hour, then the temperature was raised at 0.9° C./minute to 288° C. The catalyst precursor was held at 288° C. for 4 hours, and then was cooled to room temperature to provide the activated catalyst. The activated catalyst was maintained under PDO until hydrogenation.

A 21 ml volume of the activated catalyst having a catalyst density of 0.57 g/cm$^3$ and a void fraction of 0.42 was loaded into a batch hydrogenation wire basket to provide a catalyst charge of 12.0 grams, which was then topped with a ⅛" layer of inert denstone to prevent the catalyst from moving during hydrogenation. The basket containing the catalyst was then secured in the cooling coils of a batch hydrogenation reactor. The catalyst was then rinsed three times with deionized nitrogen sparged water.

The catalyst was then subjected to 15 batch hydrogenation cycles (run stopped after cycle 15 due to low catalyst activity), each cycle lasting 120 minutes. Importantly, the catalyst was not renewed or refreshed between batches, so each batch sequentially aged the catalyst. After each batch cycle the hydrogenation reactor was drained then loaded with 300 ml of an aqueous HPA/PDO feed mixture containing 1% n-butanol by weight. The feed mixture of aqueous HPA/PDO for the 15 batch hydrogenation cycles was mixed as shown in Table 1 above. The HPA content of the HPA feed was as described above with respect to Table 1. The hydrogenation was then conducted as described in Example 2 above.

The initial HPA content, final HPA content, and amount of HPA converted by the catalyst are shown in Table 7. Table 7 also shows the HPA conversion rate initially and the average HPA conversion rate for cycles 13-15 (catalyst activity after 24 hours of exposure to hydrogenation conditions, for hours 24-30). Finally, Table 7 shows the initial PDO content and the final PDO content.

TABLE 7

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1 | 1.35 | 0.00 | 4.04 | >50 | — | 19.11 | 22.00 |
| 2 | 1.35 | 0.00 | 4.05 | >50 | — | 19.56 | 21.86 |
| 3 | 1.94 | 0.06 | 5.67 | 51.2 | — | 17.43 | 20.81 |
| 4 | 2.14 | 0.11 | 6.11 | 46.0 | — | 17.35 | 21.08 |
| 5 | 2.08 | 0.18 | 5.72 | 35.8 | — | 17.39 | 20.96 |
| 6 | 2.39 | 0.25 | 6.42 | 31.5 | — | 19.08 | 22.16 |
| 7 | 2.08 | 0.18 | 5.72 | 35.8 | — | 17.39 | 20.96 |
| 8 | 2.39 | 0.25 | 6.42 | 31.5 | — | 19.08 | 22.16 |
| 9 | 2.76 | 0.78 | 5.94 | 18.7 | — | 15.47 | 19.27 |
| 10 | 3.11 | 1.05 | 6.19 | 14.8 | — | 15.11 | 18.82 |
| 11 | 3.15 | 1.37 | 5.35 | 11.3 | — | 15.50 | 18.43 |
| 12 | 3.23 | 1.57 | 4.97 | 10.1 | — | 16.14 | 18.84 |
| 13 | 3.39 | 2.67 | 2.15 | 4.8 | 4.8 | 13.16 | 15.74 |
| 14 | 4.27 | 2.92 | 4.04 | 5.1 | 4.8 | 12.85 | 15.06 |
| 15 | 4.29 | 3.14 | 3.14 | 4.4 | 4.8 | 12.81 | 14.93 |
| 16 | 0 | 0 | 0 | — | — | — | — |
| 17 | 0 | 0 | 0 | — | — | — | — |
| 18 | 0 | 0 | 0 | — | — | — | — |
| 19 | 0 | 0 | 0 | — | — | — | — |

Figure 7:
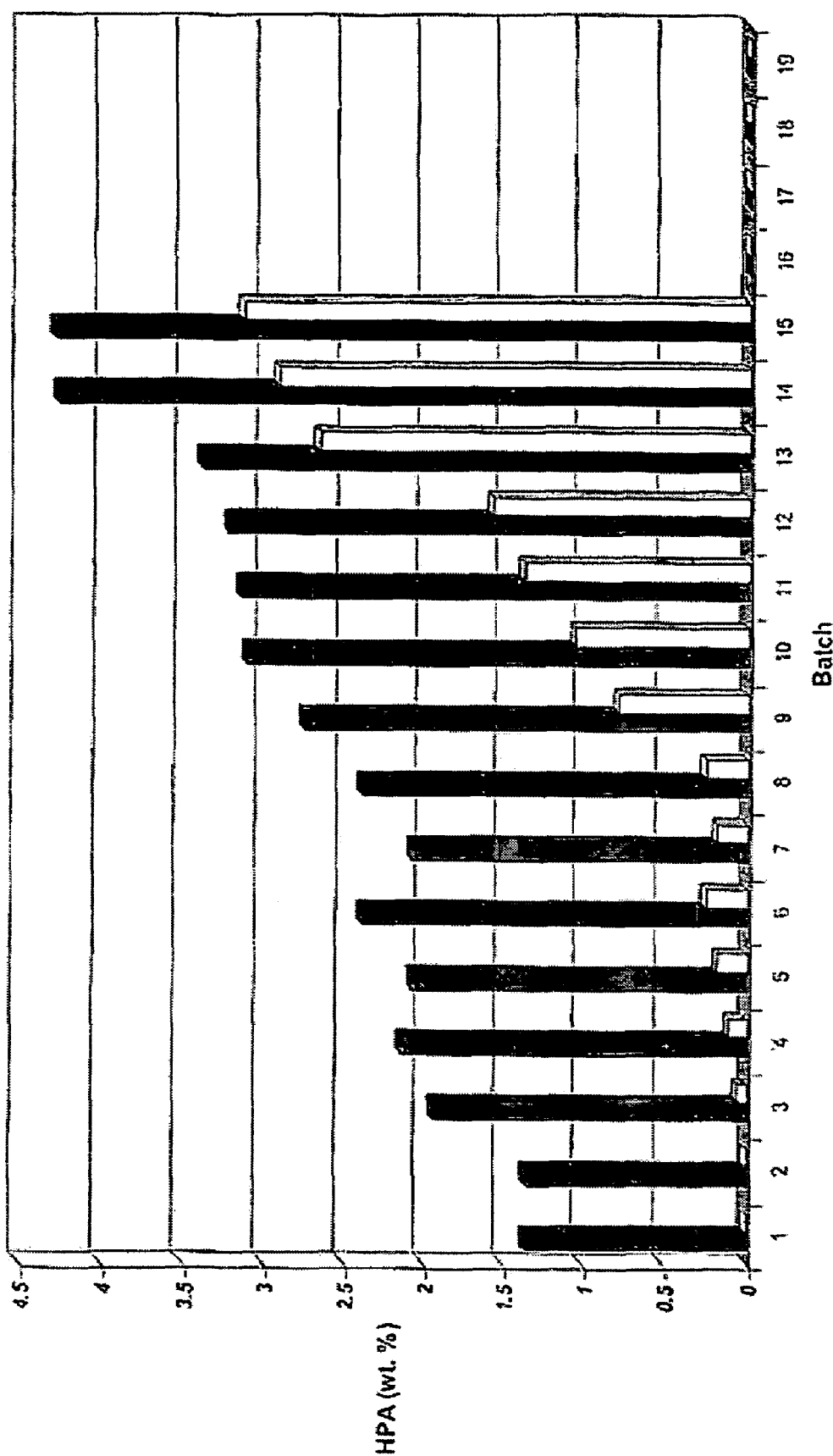
FIG. 7 is a graph showing the HPA hydrogenation catalytic activity for a series of sequential batch reactions of a catalyst not of the present invention formed of an α-alumina support with 2.5 wt. % nickel deposited on the support, and 1 wt. % ruthenium deposited on the nickel and the support.

FIG. 7 provides a graphical representation of the catalytic activity of the catalyst for hydrogenating HPA over time. The initial HPA concentration of the reaction mixture (as wt. %), shown as black bars, and the final HPA concentration of the reaction mixture (as wt. %), shown as white bars, are compared for each batch. As shown in FIG. 7, particularly compared with FIGS. 2-5, the catalyst having nickel deposited on an α-alumina support and then having ruthenium deposited on the nickel and the support was not as effective in converting HPA over the entire set of batches as the catalysts prepared according to the present invention where nickel was deposited on an α-alumina support first, and then ruthenium and rhenium were deposited on the nickel and the support.

EXAMPLE 8

For comparative purposes, hydrogenation of HPA to PDO was effected with a catalyst not of the present invention having nickel deposited on an α-alumina support, and rhenium deposited on the nickel and the support in a second impregnation. The catalyst contained 5 wt. % nickel, and 2 wt. % rhenium and contained no ruthenium (the ratio of Ni to added metals was 2.5:1 as before, however, the higher metal loading should provide greater activity).

Gamma-alumina tri-lobe pellets were calcined at 1275° C. to prepare the dry α-alumina support. An aqueous nickel solution was prepared by dissolving 3.5 grams of ammonium carbonate and 6.75 grams of nickel carbonate in an ammonium hydroxide solution (25%) to a total volume of 20 ml with moderate heat and stirring. 50 grams of the α-alumina support was impregnated with the nickel solution, absorbing 100% of the solution volume. The nickel-solution impregnated support was then aged for 1 hour at room temperature. The nickel-impregnated support was then dried at 150° C. for 3 hours, and then calcined at 453° C. for 1 hour in air.

An aqueous solution of rhenium was also prepared. 1.6 grams of ammonium perrhenate ($NH_4ReO_4$) was dissolved in deionized water to a total volume of 20 ml with heating and stirring. The calcined nickel-impregnated support was then impregnated with 98% by volume of the aqueous solution of rhenium, and aged at room temperature for 1 hour. The nickel/rhenium-impregnated support was then dried at 200° C. for 2 hours in air to form the catalyst precursor.

The catalyst precursor was activated by heating the catalyst precursor under flowing hydrogen. The catalyst precursor was heated to 107° C. by raising the temperature from ambient at 0.4° C./minute. The catalyst precursor was held at 107° C. for 1 hour, then the temperature was raised at 0.9° C./minute to 288° C. The catalyst precursor was held at 288° C. for 4 hours, and then was cooled to room temperature to provide the activated catalyst. The activated catalyst was maintained under PDO until hydrogenation.

A 21 ml volume of the activated catalyst having a catalyst density of 0.66 g/cm$^3$ and a void fraction of 0.42 was loaded into a batch hydrogenation wire basket to provide a catalyst charge of 13.8 grams, which was then topped with a ⅛" layer of inert denstone to prevent the catalyst from moving during hydrogenation. The basket containing the catalyst was then secured in the cooling coils of a batch hydrogenation reactor. The catalyst was then rinsed three times with deionized nitrogen sparged water.

The catalyst was then subjected to 19 batch hydrogenation cycles, each cycle lasting 120 minutes. Importantly, the catalyst was not renewed or refreshed between batches, so each batch sequentially aged the catalyst. After each batch cycle the hydrogenation reactor was drained then loaded with 300 ml of an aqueous HPA/PDO feed mixture containing 1% n-butanol by weight. The feed mixture of aqueous HPA/PDO for the 19 batch hydrogenation cycles was mixed as shown in Table 1 above. The HPA content of the HPA feed was as described above with respect to Table 1. The hydrogenation was then conducted as described in Example 2 above.

The initial HPA content, final HPA content, and amount of HPA converted by the catalyst are shown in Table 8. Table 8 also shows the HPA conversion rate initially and the average HPA conversion rate for cycles 13-15 (catalyst activity after 24 hours of exposure to hydrogenation conditions, for hours 24-30). Finally, Table 8 shows the initial PDO content and the final PDO content.

TABLE 8

| Cycle | Initial HPA (wt. %) | Final HPA (wt. %) | HPA converted (g) | HPA conversion rate (ml/ml · hr) | Average HPA conversion rate cycles 13-15 (ml/ml · hr) | Initial PDO (wt. %) | Final PDO (wt. %) |
|---|---|---|---|---|---|---|---|
| 1 | 1.96 | 0.00 | 5.89 | >50 | — | 18.17 | 21.35 |
| 2 | 1.73 | 0.00 | 5.20 | >50 | — | 19.17 | 20.92 |
| 3 | 1.67 | 0.00 | 5.02 | >50 | — | 19.48 | 21.62 |
| 4 | 1.63 | 0.00 | 4.90 | >50 | — | 20.42 | 22.72 |
| 5 | 2.30 | 0.00 | 6.91 | >50 | — | 17.39 | 20.22 |
| 6 | 2.21 | 0.10 | 6.34 | 43.5 | — | 16.82 | 20.19 |
| 7 | 2.22 | 0.12 | 6.30 | 40.8 | — | 16.91 | 19.76 |
| 8 | 2.50 | 0.17 | 6.99 | 36.8 | — | 18.81 | 21.92 |
| 9 | 2.92 | 0.57 | 7.07 | 23.1 | — | 14.95 | 18.58 |
| 10 | 3.29 | 0.79 | 7.50 | 19.9 | — | 14.55 | 18.68 |
| 11 | 3.51 | 0.93 | 7.74 | 17.2 | — | 15.31 | 18.83 |
| 12 | 3.57 | 1.10 | 7.40 | 15.9 | — | 16.11 | 19.63 |
| 13 | 3.99 | 1.81 | 6.54 | 11.6 | 9.9 | 13.34 | 16.66 |
| 14 | 4.83 | 2.10 | 8.20 | 9.3 | 9.9 | 13.70 | 16.31 |
| 15 | 4.48 | 2.25 | 6.70 | 9.0 | 9.9 | 13.13 | 16.23 |
| 16 | 1.73 | 0.42 | 3.92 | 19.3 | — | 18.74 | 20.69 |
| 17 | 1.57 | 0.30 | 3.81 | 21.9 | — | 18.93 | 21.34 |
| 18 | 1.57 | 0.29 | 3.85 | 22.8 | — | 19.80 | 21.54 |
| 19 | 1.62 | 0.28 | 4.02 | 24.2 | — | 20.46 | 22.52 |

Figure 8:
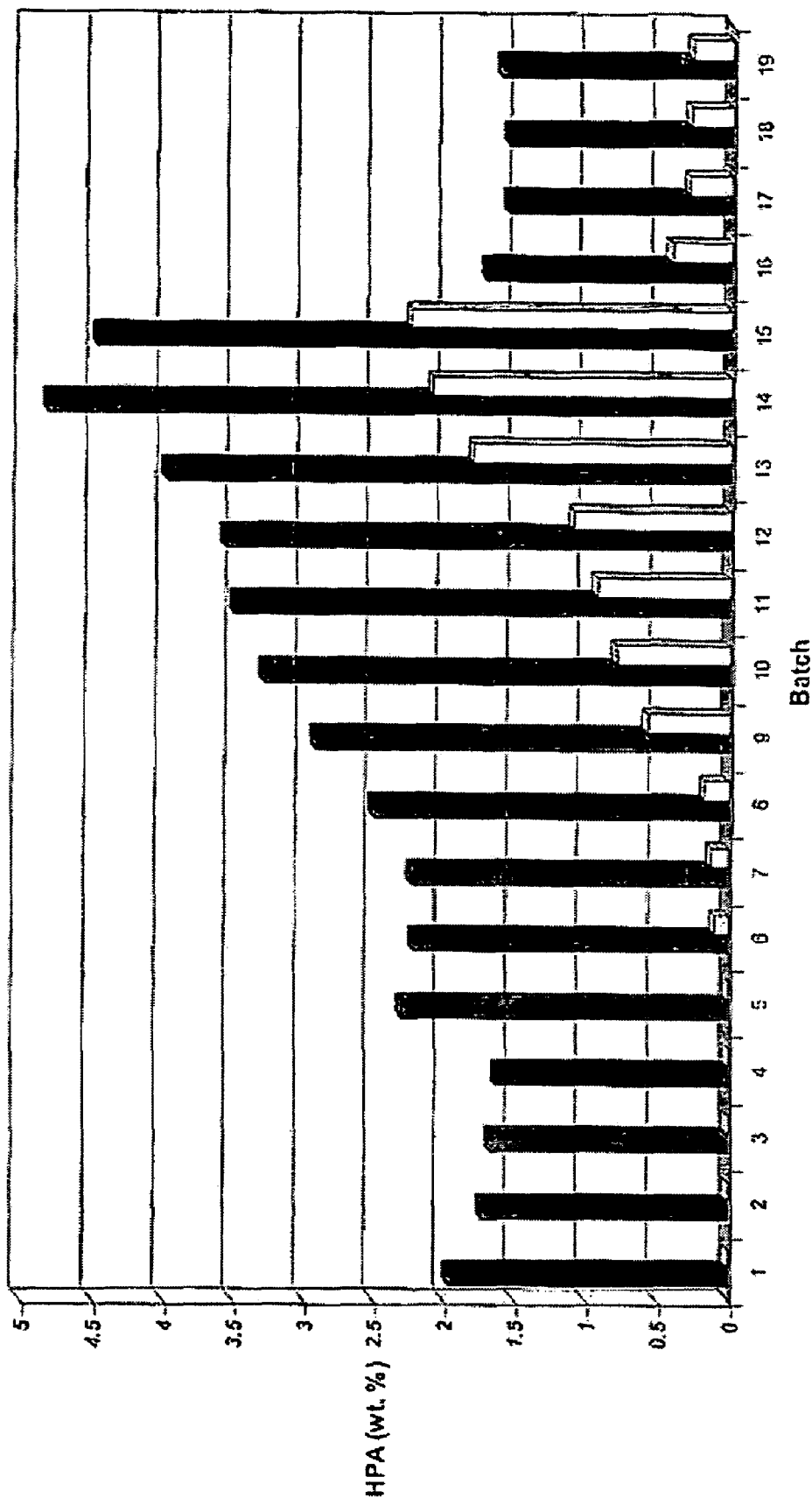
FIG. 8 is a graph showing the HPA hydrogenation catalytic activity for a series of sequential batch reactions of a catalyst not of the present invention formed of an α-alumina support with 2.5 wt. % nickel deposited on the support, and 1 wt. % rhenium deposited on the nickel and the support.

FIG. 8 provides a graphical representation of the catalytic activity of the catalyst for hydrogenating HPA over time. The initial HPA concentration of the reaction mixture (as wt. %), shown as black bars, and the final HPA concentration of the reaction mixture (as wt. %), shown as white bars, are compared for each batch. As shown in FIG. 8, particularly compared with FIGS. 2-5, the catalyst having nickel deposited on an α-alumina support and then having rhenium deposited on the nickel and the support was not as effective in converting HPA over the entire set of batches as the catalysts prepared according to the present invention where nickel was deposited on an α-alumina support first, and then ruthenium and rhenium were deposited on the nickel and the support.

EXAMPLE 9

The crush strength of fresh catalyst of the present invention was measured, where the catalyst had the structure of nickel deposited on an α-alumina support, and ruthenium and rhenium deposited on the nickel and the support. The catalyst contained 2.5 wt. % nickel, 1 wt. % ruthenium, and 1 wt. % rhenium.

Gamma alumina tri-lobe pellets were calcined at 1275° C. to prepare the α-alumina support. An aqueous nickel solution was prepared by dissolving 1.77 grams of ammonium carbonate in ammonium hydroxide solution (25%) with moderate heat and stirring, followed by the addition and dissolution of 3.4 grams of nickel carbonate in the ammonium carbonate/ammonium hydroxide solution to a total solution volume of 20 ml. 50 grams of the α-alumina support was impregnated with the nickel solution, absorbing 100% of the solution volume. The nickel-solution impregnated support was then aged for 1 hour at room temperature. The nickel-impregnated support was then dried at 150° C. for 3 hours, and then calcined at 453° C. for 1 hour in air.

An aqueous solution of ruthenium and rhenium was also prepared. 0.8 grams of ammonium perrhenate was dissolved in deionized water with low heat and stirring. 1.5 grams of ruthenium trichloride was then added and dissolved in the ammonium perrhenate solution with heating and stirring to provide a total solution volume of 20 ml. The calcined nickel-impregnated support was then impregnated with the total volume of the aqueous solution of ruthenium and rhenium, and aged for 1 hour at room temperature. The nickel/ruthenium-rhenium impregnated support was then dried at 200° C. for 2 hours in air to form the catalyst precursor.

The catalyst precursor was activated by heating the catalyst precursor under flowing hydrogen. The catalyst precursor was heated to 107° C. by raising the temperature from ambient at 0.4° C./minute. The catalyst precursor was held at 107° C. for 1 hour, then the temperature was raised at 0.9° C./minute to 288° C. The catalyst precursor was held at 288° C. for 4 hours, and then was cooled to room temperature to provide the activated catalyst.

The crush strength of the activated catalyst was measured. 42 catalyst pellets were randomly selected and manually sieved through a U.S. Standard Sieve No. 20 (ASTM) to remove dust, fines, and small pieces. The total length of each pellet was measured with calipers and recorded. The crush strength of each pellet was then measured by placing the pellet in a Side Crush Measurement instrument between upper and lower horizontal crushing plates in a radial orientation, then applying and gradually increasing force on the pellet by the upper and lower crushing plates until the pellet crushed. The force at which each pellet was crushed was recorded. The crush strength (per unit length) of the catalyst was calculated as the sum of the individual pellet crush strength measurements divided by the sum of all individual length measurements: Crush strength=Σ(all individual crush strength measurements)/Σ(all individual length measurements).

The crush strength of the fresh catalyst was calculated to be 2.85 kg/mm.

EXAMPLE 10

The crush strength of spent catalyst of the present invention was measured, where the catalyst had the structure of nickel deposited on an α-alumina support, and ruthenium and rhenium deposited on the nickel and the support. The catalyst contained 2.5 wt. % nickel, 1 wt. % ruthenium, and 1 wt. % rhenium.

Gamma-alumina tri-lobe pellets were calcined at 1275° C. to prepare the α-alumina support. An aqueous nickel solution was prepared by dissolving 3.54 grams of ammonium carbonate in ammonium hydroxide solution (25%) with moderate heat and stirring, followed by the addition and dissolution of 6.8 grams of nickel carbonate in the ammonium carbonate/ammonium hydroxide solution to a total solution volume of 40 ml. 100 grams of the α-alumina support was impregnated with the nickel solution, absorbing 100% of the solution volume. The nickel-solution impregnated support was then aged for 1 hour at room temperature. The nickel-impregnated support was then dried at 150° C. for 3 hours, and then calcined at 453° C. for 1 hour in air.

An aqueous solution of ruthenium and rhenium was also prepared. 1.6 grams of ammonium perrhenate was dissolved in deionized water with low heat and stirring. 3.0 grams of ruthenium trichloride was then added and dissolved in the ammonium perrhenate solution with heating and stirring to provide a total solution volume of 40 ml. The calcined nickel-impregnated support was then impregnated with the total volume of the aqueous solution of ruthenium and rhenium, and aged for 1 hour at room temperature. The nickel/ruthenium-rhenium impregnated support was then dried at 200° C. for 2 hours in air to form the catalyst precursor.

The catalyst precursor was activated by heating the catalyst precursor under flowing hydrogen. The catalyst precursor was heated to 107° C. by raising the temperature from ambient at 0.4° C./minute. The catalyst precursor was held at 107° C. for 1 hour, then the temperature was raised at 0.9° C./minute to 288° C. The catalyst precursor was held at 288° C. for 4 hours, and then was cooled to room temperature to provide the activated catalyst.

18.65 grams (dry basis) of the activated catalyst having a catalyst volume of 30 ml were loaded into a catalyst bed having a length of 21.6 cm, and the catalyst was used to catalyze the hydrogenation of HPA to PDO at a liquid hourly space velocity of 1.62 1/hr, at a temperature varied from 50° C. to 150° C. depending on HPA concentration in the feed, and a hydrogen pressure of 8.47 MPa. The run was for a period of 1897 hours to produce 6730 grams of PDO.

Spent catalyst was removed from the catalyst bed and the crush strength of the spent catalyst was measured. 44 catalyst pellets were randomly selected and manually sieved through a U.S. Standard Sieve No. 20 (ASTM) to remove dust, fines, and small pieces. The total length of each pellet was measured with calipers and recorded. The crush strength of each pellet was then measured by placing the pellet in a Side Crush Measurement instrument between upper and lower horizontal crushing plates in a radial orientation, then applying and gradually increasing force on the pellet by the upper and lower crushing plates until the pellet crushed. The force at which each pellet was crushed was recorded. The crush strength (per unit length) of the catalyst was calculated as the sum of the individual pellet crush strength measurements divided by the sum of all individual length measurements: Crush strength=Σ(all individual crush strength measurements)/Σ(all individual length measurements).

The crush strength of the spent catalyst was calculated to be 2.4 kg/mm.

Further variations and modifications of the invention will be apparent to those skilled in the art from the foregoing, and are intended to be encompassed by the claims appended hereto.

What is claimed is:

1. A process for hydrogenating aldehydes comprising:
hydrogenating an aldehyde in the presence of a catalyst wherein the catalyst has a composition comprising a support comprising α-alumina and non-support metals comprising nickel, ruthenium, and a promoter selected from the group consisting of rhenium, tungsten, molybdenum, chromium, lanthanum, tin, iron, cobalt, silver, copper or mixtures thereof;
wherein the nickel contacts the support and the ruthenium and the promoter at least partially overlay the nickel.

2. The process of claim 1 wherein the non-support metals comprise no more than 8 wt. % of the catalyst.

3. The process of claim 1 wherein the catalyst contains up to 6.0 wt. % nickel.

4. The process of claim 1 wherein the weight ratio of nickel to ruthenium plus promoter in the catalyst is from 1:2 to 6:1.

5. The process of claim 1 wherein the catalyst contains from 0.1 wt. % to 3.5 wt. % ruthenium and from 0.1 wt. % to 3.5 wt. % promoter and the weight ratio of ruthenium to promoter is from 1:4 to 4:1.

6. The process of claim 1 wherein said non-support metals of said catalyst further comprise molybdenum wherein said molybdenum is alloyed with said nickel and said ruthenium and said promoter at least partially overlay said molybdenum and said nickel.

7. The process of claim 1 wherein the promoter is rhenium.

8. The process of claim 1 wherein said aldehyde is a hydroxyaldehyde.

9. The process of claim 1 wherein said aldehyde is 3-hydroxypropionaldehyde, and said 3-hydroxypropionaldehyde is hydrogenated to 1,3-propanediol.

10. The process of claim 9 wherein the catalyst has an activity sufficient to hydrogenate 3-hydroxypropionaldehyde at a rate of at least 25 ml 3-hydroxypropionaldehyde/ml catalyst.hr at a temperature of from 50° C. to 190° C., at a pH of from 4.0 to 6.5, and at a hydrogen pressure of from 6.89 MPa to 11.0 MPa after at least 24 hours of catalyzing hydrogenation at a temperature of from 50° C. to 190° C., at a pH of from 4.0 to 6.5, and at a hydrogen pressure of from 6.89 MPa to 11.0 MPa.

11. The process of claim 9 wherein 3-hydroxypropionaldehyde is hydrogenated to 1,3-propanediol under a hydrogen atmosphere at a pressure of from 6.89 MPa to 11.0 MPa, at a temperature of from 50° C. to 190° C., and at a pH of less than 6.5.

12. The process of claim 9 wherein the 3-hydroxypropionaldehyde is in an aqueous solution where the 3-hydroxypropionaldehyde comprises at most 15 wt. % of the aqueous solution.

13. A hydrogenation catalyst comprising:
a support comprising α-alumina; and
non-support metals comprising
(i) up to 6 wt. % nickel;
(ii) ruthenium; and
(iii) a promoter selected from the group consisting of rhenium, tungsten, molybdenum, chromium, lanthanum, tin, iron, cobalt, silver, copper, or mixtures thereof;
wherein the nickel contacts the support, and the ruthenium and the promoter at least partially overlay the nickel, and
wherein the non-support metals comprise no more than 8 wt % of the catalyst.

14. The hydrogenation catalyst of claim 13 wherein the catalyst contains from 1 wt. % to 3 wt. % nickel.

15. The hydrogenation catalyst of claim 13 wherein the support consists essentially of α-alumina.

16. The hydrogenation catalyst of claim 13 wherein the catalyst has a crush strength of at least 2.26 kg/mm.

17. The hydrogenation catalyst of claim 13 wherein the catalyst is a pellet having a cylindrical or a tri-lobal shape.

18. The hydrogenation catalyst of claim 13 wherein the promoter is rhenium.

19. The hydrogenation catalyst of claim 13 wherein the non-support metals include molybdenum where the molybdenum is alloyed with the nickel, and the ruthenium and the promoter at least partially overlay the nickel and the molybdenum.

20. The hydrogenation catalyst of claim 13 wherein the catalyst contains from 0.1 wt. % to 3.5 wt. % ruthenium and from 0.1 wt. % to 3.5 wt. % promoter where the weight ratio of ruthenium to promoter in the catalyst is from 1:4 to 4:1.

21. The hydrogenation catalyst of claim 13 wherein the weight ratio of nickel to ruthenium plus promoter in the catalyst is from 1:2 to 6:1.

22. The hydrogenation catalyst of claim 13 wherein said catalyst has an activity effective to hydrogenate 3-hydroxypropionaldehyde at a rate of at least 25 ml 3-hydroxypropionaldehyde/ml catalyst.hr at a temperature of from 50° C. to 190° C., at a pH of from 4.0 to 6.5, and at a pressure of from 6.89 MPa to 11.0 MPa after at least 24 hours of catalyzing hydrogenation at a temperature of from 50° C. to 190° C., at a pH of from 4.0 to 6.5, and at a hydrogen pressure of from 6.89 MPa to 11.0 MPa.

23. The hydrogenation catalyst of claim 22 wherein said activity is at least 35 ml 3-hydroxypropionaldehyde/ml catalyst.hr.

24. The hydrogenation catalyst of claim 13 wherein the catalyst is stable in air at ambient conditions.

25. A process for preparing a catalyst comprising:
a) depositing nickel on a support comprised of α-alumina;
b) calcining the support with the nickel thereon;
c) after calcining, depositing ruthenium and a promoter selected from the group consisting of rhenium, tungsten, molybdenum, chromium, lanthanum, tin, iron, cobalt, silver, copper, or mixtures thereof on the support and on the nickel to form a catalyst precursor; and
d) reducing the nickel, ruthenium, and promoter of the catalyst precursor to a metallic zero oxidation state to form the catalyst.

26. The process of claim 25 wherein the nickel, ruthenium, and promoter of the catalyst precursor are reduced by holding the catalyst precursor under a hydrogen atmosphere at a temperature of from 100° C. to 500° C. for a period of from 20 minutes to 24 hours.

27. The process of claim 25 wherein the nickel is deposited on the support by impregnating the support with an aqueous solution containing said nickel.

28. The process of claim 25 wherein the ruthenium and the promoter are deposited on the support and on the nickel by impregnating the support with the nickel thereon with an aqueous solution containing said ruthenium and said promoter.

29. The process of claim 25 wherein said promoter is rhenium.

30. The process of claim 25 wherein the support consists essentially of α-alumina.

31. The process of claim 25 wherein a concentration of nickel is deposited on the support sufficient to provide a concentration of nickel, by metallic weight, of up to 6 wt. % of the catalyst.

32. The process of claim 25 wherein the nickel, ruthenium, and promoter deposited on the support comprise no more than 8 wt. % of the catalyst.

* * * * *